United States Patent
Iizuka et al.

(10) Patent No.: US 10,494,659 B2
(45) Date of Patent: Dec. 3, 2019

(54) PROCESS FOR PRODUCING SUBSTRATE SOLUTION FOR MEASURING LIPASE ACTIVITY, AND METHOD FOR SIMPLIFYING PRODUCTION

(71) Applicant: SHINO-TEST CORPORATION, Tokyo (JP)

(72) Inventors: Naomi Iizuka, Sagamihara (JP); Atsushi Hikichi, Sagamihara (JP)

(73) Assignee: Shino-Test Corporation, Tokyo (JP)

( * ) Notice: Subject to any disclaimer, the term of this patent is extended or adjusted under 35 U.S.C. 154(b) by 0 days.

(21) Appl. No.: 15/430,106

(22) Filed: Feb. 10, 2017

(65) Prior Publication Data

US 2017/0152544 A1    Jun. 1, 2017

Related U.S. Application Data

(63) Continuation-in-part of application No. PCT/JP2015/072543, filed on Aug. 7, 2015.

(30) Foreign Application Priority Data

Aug. 12, 2014 (JP) ................. 2014-164107

(51) Int. Cl.
*C12Q 1/44* (2006.01)
*C12N 9/20* (2006.01)

(52) U.S. Cl.
CPC ............... *C12Q 1/44* (2013.01); *C12N 9/20* (2013.01); *C12Y 301/01003* (2013.01); *G01N 2333/92* (2013.01)

(58) Field of Classification Search
CPC .............. C12Q 1/44; C12Y 301/01003; G01N 2333/92
See application file for complete search history.

(56) References Cited

U.S. PATENT DOCUMENTS

| 4,847,376 A | 7/1989 | Neumann et al. |
| 4,988,497 A | 1/1991 | Neumann et al. |

(Continued)

FOREIGN PATENT DOCUMENTS

| EP | 0337005 | 10/1989 |
| JP | 58-156330 | 9/1983 |

(Continued)

OTHER PUBLICATIONS

Validation and diagnostic efficacy of a lipase assay using the substrate 1,2-o-dilauryl-rac-glycero glutaric acid-(6' methyl resorufin)-ester for the diagnosis of acute pancreatitis in dogs Roberta Graca, Joanne Messick, Sheila McCullough, Anne Barger, Walter Hoffman Vet. Clin. Pathol. 34(1) 39-43 (Year: 2005).*

(Continued)

*Primary Examiner* — Krishnan S Menon
*Assistant Examiner* — Dwan A Gerido
(74) *Attorney, Agent, or Firm* — McCarter & English, LLP

(57) ABSTRACT

Provided is a process for producing a substrate solution for measuring lipase activity including, as a substrate for measuring lipase activity, 1,2-o-dilauryl-rac-glycero-3-glutaric acid (6'-methylresorufin) ester, wherein the production process does not necessitate cumbersome or special processing such that skill is required, or does not necessitate a special apparatus, instruments, or other items. This production process is a process for producing a substrate solution for measuring lipase activity, and is characterized by including the steps of (1) mixing the substrate for measuring lipase activity and a side-chain-type nonreactive polyether-modified-type modified silicone oil or a polyoxyethylene/polyoxypropylene condensate to prepare a mixture, and (2) mixing all or a portion of the mixture of step (1) with water or an aqueous solution.

1 Claim, 1 Drawing Sheet

(56) References Cited

U.S. PATENT DOCUMENTS

| | | | |
|---|---|---|---|
| 5,082,769 A * | 1/1992 | Miki | C12Q 1/44 |
| | | | 435/18 |
| 6,322,993 B1 | 11/2001 | Schelong et al. | |
| 7,514,255 B2 * | 4/2009 | Huth | C12Q 1/34 |
| | | | 435/18 |
| 8,216,799 B2 * | 7/2012 | Kageyama | C12Q 1/44 |
| | | | 435/18 |
| 9,145,577 B2 * | 9/2015 | Jin | C12Q 1/44 |

FOREIGN PATENT DOCUMENTS

| | | |
|---|---|---|
| JP | 61-254197 | 11/1986 |
| JP | 63-188398 | 8/1988 |
| JP | 9-215500 | 8/1997 |
| JP | 11-504529 | 4/1999 |
| JP | 11-318494 | 11/1999 |
| JP | 2002-369681 | 12/2002 |
| JP | 2006-180741 | 7/2006 |
| JP | 2006-191863 | 7/2006 |
| WO | 2010/107560 | 9/2010 |

OTHER PUBLICATIONS

Kanai's Manual of Clinical Laboratory Medicine, 30th Ed., edited by Masamitsu Kanai, publiished by Kanehara & Co., Ltd., on Aug. 20, 1993, pp. 670-674 (with Partial English Translation).
Kanai's Manual of Clinicai Laboratory Medicine., 33rd Ed., edited by Masamitsu Kanai, publiished by Kanehara & Co., Ltd., on Apr. 1, 2010, pp. 545-547 (with Partial English Translation).
European Supplementary Serarch Report dated Nov. 22, 2017 based on co-pending European Application No. 15832348.5, 8 Pages.

* cited by examiner

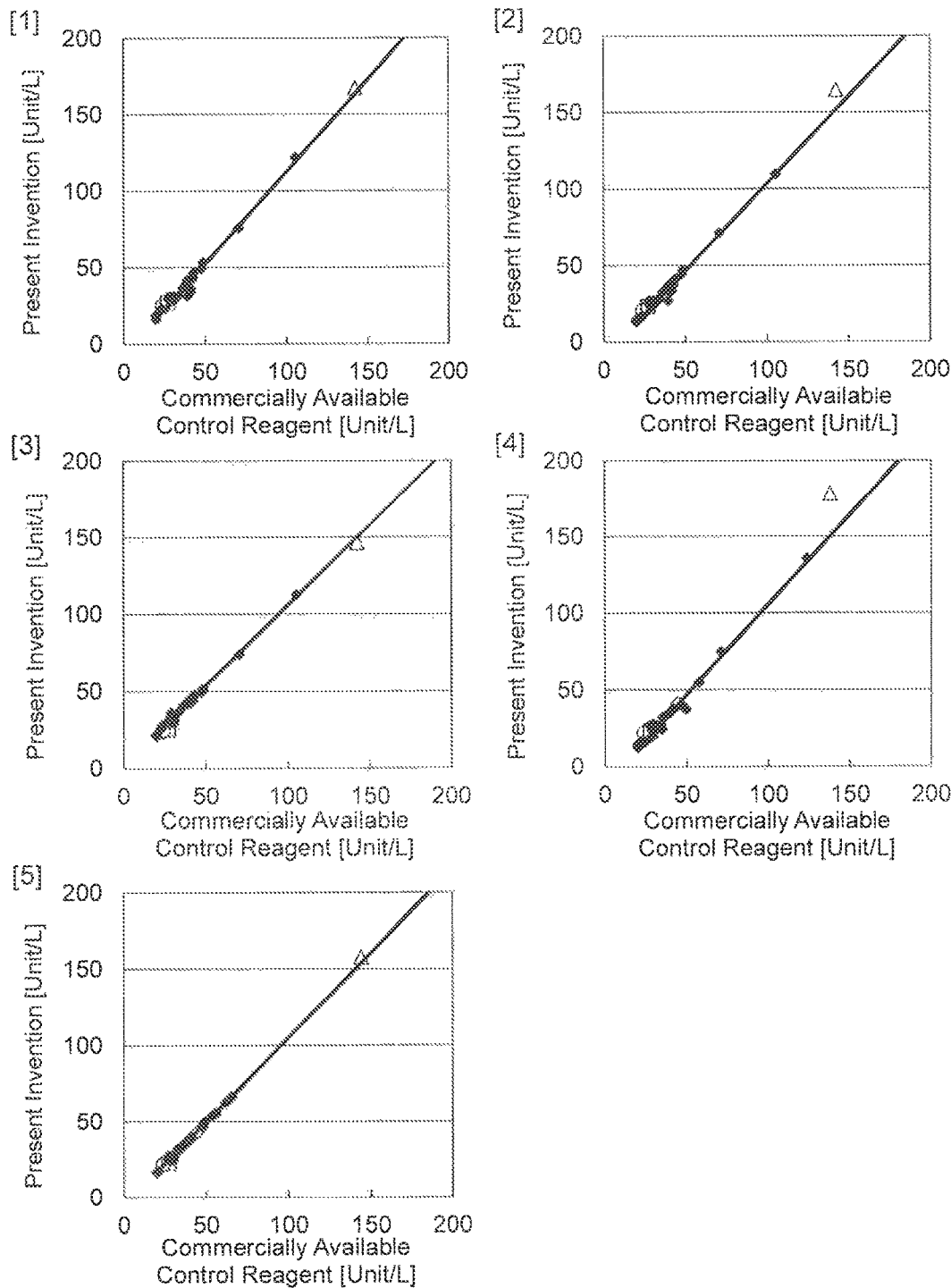

PROCESS FOR PRODUCING SUBSTRATE SOLUTION FOR MEASURING LIPASE ACTIVITY, AND METHOD FOR SIMPLIFYING PRODUCTION

RELATED APPLICATIONS

This application is a continuation-in-part of International Application PCT/JP2015/072543, with a filing date of Aug. 7, 2015, which claims the benefit of Japanese Patent Application No. 2014-164107, with a filing date of Aug. 12, 2014, both of which are incorporated herein, in entirety, by reference.

TECHNICAL FIELD

The present invention relates to a process for producing a substrate solution used for measuring lipase activity in a sample. The process can make the production of the substrate solution simpler than conventional methods.

In addition, the present invention also relates to a method for simplifying production of the substrate solution as in the above production process.

The present invention is useful in the fields of life sciences (e.g., clinical laboratory tests) and chemistry (e.g., analytical chemistry).

BACKGROUND ART

Lipase activity in serum or plasma is increased in pancreatic diseases (e.g., acute and chronic pancreatitis or pancreatic cancer), so that the lipase activity is a useful marker for the pancreatitis, etc.

The lipase is an enzyme that catalyzes a reaction in which ester bonds (at α-position (positions 1 and 3)) of a triglyceride (TG) (three long-chain fatty acid molecules are each linked via an ester bond to glycerol) are hydrolyzed to produce two fatty acid molecules and one β-monoglyceride molecule.

This one β-monoglyceride molecule is isomerized to α-monoglyceride, which is then hydrolyzed by the lipase to produce a glycerol and a fatty acid.

Examples of an assay for measuring lipase activity in serum or plasma include the following assays (see Non Patent Documents 1 and 2).

The examples known include a Cherry-Crandall method in which an olive oil emulsion is used as a lipase substrate; this olive oil emulsion is made to contact and react with, for example, a serum sample at 37° C. for 24 hours; and then a fatty acid, which has been generated through hydrolysis by the lipase, is titrated with an alkali.

In this method, however, the reaction time is long, the lipase of interest can be inactivated, and the reaction is thus markedly inhibited.

Another example known is a Vogel-Zieve method and a modified method thereof in which a triolein or olive oil emulsion is used as a lipase substrate; this triolein or olive oil emulsion is made to contact and react with, for example, a serum sample; the emulsified micelles are then hydrolyzed by the lipase to cause a decrease in turbidity of the resulting reaction solution; and the lipase activity is determined from the decrease.

These methods, however, involve serum protein-mediated inhibition and/or interference due to rheumatoid factor-induced aggregation, so that it is difficult to produce a uniform and stable emulsion. Also, the methods are poorly reproducible and thus disadvantageous.

Another example known is an assay for measuring lipase activity in which BALB (2,3-dimercapto-1-propanol tributyrate) is used as a lipase substrate; this BALB is made to contact and react with, for example, a serum sample; BAL (2,3-dimercapto-1-propanol), which has been generated through hydrolysis by the lipase, is reacted with DTNB (5,5'-dithiobis-2-nitrobenzoic acid); and yellow light emitted by the resulting TNB anion is measured at 412 nm.

This assay, however, involves interference with a liver esterase under highly concentrated conditions. Accordingly, the liver esterase is mixed through a reaction cell or a nozzle (probe) from an assay reagent for measuring another item. This affects a measured value and causes an error, so that this assay is thus disadvantageous.

Another example known is an assay for measuring lipase activity in which 1,2-dilinoleoyl glycerol, which is a natural substrate, is used as a lipase substrate; this 1,2-dilinoleoyl glycerol is made to contact and react with, for example, a serum sample: linoleic acid, which has been generated through hydrolysis by the lipase, cooperates, in the presence of Coenzyme A, $NAD^+$, and ATP, with acyl-CoA synthetase, Acyl-CoA oxidase, and an enoyl-CoA hydratase-3-hydroxyacyl-CoA dehydrogenase-3-ketoacyl-CoA thiolase multienzyme complex to perform β-oxidation; and then the NADH production rate when the β-oxidation occurs is measured.

This assay, however, also involves interference with a liver esterase under highly concentrated conditions. Accordingly, the liver esterase is mixed through a reaction cell or a nozzle (probe) from an assay reagent for measuring another item. This affects a measured value and causes an error, so that this assay is thus disadvantageous.

In addition to the above respective assays, an assay for measuring lipase activity in serum or plasma has been developed in which 1,2-o-dilauryl-rac-glycero-3-glutaric acid (6'-methylresorufin) ester (DGGMR) is used as a lipase substrate (see Patent Document 1 and Non Patent Document 2).

In this assay, 1,2-o-dilauryl-rac-glycero-3-glutaric acid (6'-methylresorufin) ester (hereinafter, sometimes referred to as "DGGMR") is made to contact and react with, for example, a serum sample; and the lipase catalyzes hydrolysis to generate 1,2-o-dilauryl-rac-glycerol and glutaric acid (6'-methylresorufin) ester.

This glutaric acid (6'-methylresorufin) ester is unstable and is hydrolyzed readily and naturally to generate 6'-methylresorufin (λmax: 580 nm).

An increase in the 6'-methylresorufin generated is measured by reading absorbance at or near 580 nm. By doing so, the lipase activity value in the sample can be determined.

This assay for measuring lipase activity using DGGMR as a lipase substrate is simple because the measurement proceeds in a series of reactions. Besides, the assay is also advantageous because the assay is unlikely to be affected by an esterase mixed through a reaction cell or a nozzle (probe) from other measuring reagents.

Meanwhile, a lipase contained in, for example, serum or plasma is most efficient at a water-oil interface of an emulsified triglyceride substrate. The reaction rate of this lipase involves the surface area of the substrate dispersed. Thus, for measuring the lipase activity, it seems critical to prepare a substrate composed of stable and uniform micelle particles (see Non Patent Document 2).

For this purpose, when a substrate solution (substrate solution for measuring lipase activity) used for measuring lipase activity is produced conventionally, the substrate solution should be emulsified and composed of stable and uniform micelle particles. To realize this, various methods have been taken into consideration: a substrate may be mixed into an aqueous solution containing a surfactant; a substrate may be mixed into a solution containing an organic solvent (e.g., an alcohol); a substrate-containing liquid may be added dropwise and mixed into a solution; a substrate-containing liquid may be jet-injected into a solution; a substrate solution may be stirred with a powerful mixer at a high speed; or a substrate solution may be subject to ultrasonication. The methods necessitate cumbersome or special processing such that skill is required. The methods also necessitate a special apparatus, instruments, or other items.

For example, disclosed is a process for producing a transparent miscible aqueous solution containing a water-insoluble substance, characterized in that a water-insoluble substance (e.g., triglyceride) as a lipase substrate is added to an aqueous solution containing a nonionic surfactant; the mixture is heated while being stirred; the temperature is once raised to a temperature higher than the clouding point of the nonionic surfactant; and the temperature is then cooled to a temperature equal to or less than the clouding point while the mixture is further stirred (see Patent Document 2).

Also disclosed is a transparent triglyceride substrate solution for measuring lipase activity, characterized in that an aqueous solution containing a nonionic surfactant is heated to a temperature equal to or higher than the clouding point of the nonionic surfactant; a triglyceride is added and dissolved in the mixture while being stirred to prepare a uniform and miscible (transparent) aqueous solution containing the triglyceride; and the resulting aqueous solution is used as a lipase substrate and, as needed, further includes a lipase function promoter (see Patent Document 3).

Also disclosed is a process for producing a substrate solution used for measuring lipase activity in a sample, characterized in that when a substrate (e.g., a triglyceride) is mixed with a surfactant (e.g., a nonionic surfactant with an HLB of 10 to 16), an water-soluble organic solvent (e.g., methanol or ethanol) is mixed together; and a mixing process uses vibrations such as ultrasonication, wherein the substrate solution contains micelles with a geometric mean diameter of 0.17 µm to 0.38 µm and the geometric standard deviation of the diameter distribution of the micelles is 0.25 µm or less (see Patent Document 4).

Here, in the assay for measuring lipase activity using the DGGMR as a lipase substrate, the substrate solution is produced as follows: "b) 0.9 g of sodium taurodeoxycholate and 0.3 g of a colipase (from a pig) are dissolved under stirring in 60 ml of distilled water. While being well stirred, a solution containing 70 mg of 1,2-o-dilauryl-rac-glycero-3-glutaric acid (6-methyl-resorufin) ester in 1.7 ml of n-propanol is jet-injected into the above solution" (Example 29 of Patent Document 1); or "Reagent 2: 0.6 g of a chromogenic substrate for a lipase (e.g., 1,2-o-dilauryl-rac-glycero-3-glutaric acid (6'-methylresorufin) ester) was dissolved into 9 ml of a suitable alcohol (e.g., ethanol). Then, 1 g of an emulgator (e.g., Brij 35 or Triton X-114) was added to the solution. The resulting oelic phase was aspirated using an injection needle and was made to pass through a fine cannula (with an inner diameter of 0.15 to 1.0 mm) under a high pressure, so that the solution is pressure-injected into an aqueous solution under stirring" (Example 3 of Patent Document 5). In view of the above, an alcohol was used as an organic solvent and the assays necessitate a process in which the substrate-containing liquid is jet-injected (injected under a high pressure) into a solution.

Note that disclosed is that a substrate solution for lipase analysis contains a lipase substrate (e.g., DGGMR) as well as at least one lipase substrate solubilizer selected from an anionic surfactant, a lecithin, and a cholesterol ester. This substrate solution exerts an effect of making the substrate well miscible without decreasing the activity of the substrate (see Patent Document 6).

Then, this document describes results where when 0.1% by weight of a nonionic surfactant was used instead of the above lipase substrate solubilizer, "the solution was turbid and thus had a drawback in the measurement".

Also disclosed is a lipase substrate solution for measuring enzyme activity, characterized by containing at least a lipase substrate (e.g., DGGMR) and 1,2-diphytanoyl-sn-glycero-3-phosphocholine as a lipase substrate solubilizer. This substrate solution is very transparent. Accordingly, effects can be exerted such that the lipase activity can be measured with high accuracy and its storage stability is increased (see Patent Document 7).

PRIOR ART DOCUMENTS

Patent Documents

Patent Document 1: JP Patent Publication (Kokai) No. 61-254197A (1986)
Patent Document 2: JP Patent Publication (Kokai) No. 58-156330A (1983)
Patent Document 3: JP Patent Publication (Kokai) No. 63-188398A (1988)
Patent Document 4: JP Patent Publication (Kokai) No. 2006-180741A (2006)
Patent Document 5: JP Patent Publication (Kohyo) No. 11-504529A (1999)
Patent Document 6: JP Patent Publication (Kokai) No. 9-215500A (1997)
Patent Document 7: JP Patent Publication (Kokai) No. 11-318494A (1999)

Non Patent Documents

Non Patent Document 1: Kanai's Manual of Clinical Laboratory Medicine, 30th ed., p. 670-674, edited by KANAI, Masamitsu, published by KANEHARA & Co., Ltd., on Aug. 20, 1993.
Non Patent Document 2: Kanai's Manual of Clinical Laboratory Medicine, 33th ed., p. 545-547, edited by KANAI, Masamitsu, published by KANEHARA & Co., Ltd., on Apr. 1, 2010.

SUMMARY OF INVENTION

Objects to be Attained by the Invention

As described above, the production of the substrate solution for measuring lipase activity necessitates cumbersome or special processing such that skill is required, or necessitates a special apparatus, instruments, or other items.

By contrast, the purpose of the present invention is to provide a process for producing a substrate solution for measuring lipase activity including, as a substrate for measuring lipase activity, DGGMR, wherein the production process does not necessitate cumbersome or special processing such that skill is required, or does not necessitate a special apparatus, instruments, or other items.

In addition, another purpose of the present invention is to provide a method for simplifying production of a substrate solution for measuring lipase activity in the above production process in which DGGMR is included as a substrate for measuring lipase activity, wherein the method does not necessitate cumbersome or special processing such that skill is required, or does not necessitate a special apparatus, instruments, or other items.

Means for Attaining the Objects

The present inventors have conducted intensive research on how to produce a substrate solution for measuring lipase activity in which DGGMR is included as a substrate for measuring lipase activity. As a result, the present inventors have found out that the above problems can be solved such that DGGMR and a side-chain-type nonreactive polyether-modified-type modified silicone oil or a polyoxyethylene/polyoxypropylene condensate (hereinafter, sometimes referred to as "the present polymer") are mixed, and all or a portion of the mixture is then mixed with water or an aqueous solution. In this way, the present inventors have completed the present invention.

The present invention is summarized as follows.

<1> A process for producing a substrate solution that is used for measuring lipase activity in a sample and comprises, as a substrate for measuring lipase activity, 1,2-o-dilauryl-rac-glycero-3-glutaric acid (6'-methylresorufin) ester, the process comprising the steps of:

(1) mixing the substrate for measuring lipase activity and a side-chain-type nonreactive polyether-modified-type modified silicone oil or a polyoxyethylene/polyoxypropylene condensate to prepare a mixture; and (2) mixing all or a portion of the mixture of step (1) with water or an aqueous solution.

<2> A method for simplifying production of a substrate solution in a process for producing the substrate solution that is used for measuring lipase activity in a sample and comprises, as a substrate for measuring lipase activity, 1,2-o-dilauryl-rac-glycero-3-glutaric acid (6'-methylresorufin) ester, the method comprising the steps of:

(1) mixing the substrate for measuring lipase activity and a side-chain-type nonreactive polyether-modified-type modified silicone oil or a polyoxyethylene/polyoxypropylene condensate to prepare a mixture; and (2) mixing all or a portion of the mixture of step (1) with water or an aqueous solution.

Advantageous Effects of Invention

The process for producing a substrate solution for measuring lipase activity according to the present invention does not necessitate cumbersome or special processing such that skill is required, or does not necessitate a special apparatus, instruments, or other items. The process can produce a substrate solution for measuring lipase activity in which DGGMR is included as a substrate for measuring lipase activity.

In addition, the method for simplifying production of a substrate solution for measuring lipase activity according to the present invention does not necessitate cumbersome or special processing such that skill is required, or does not necessitate a special apparatus, instruments, or other items. The method can simplify the production of a substrate solution for measuring lipase activity in which DGGMR is included as a substrate for measuring lipase activity.

Accordingly, when the process for producing a substrate solution for measuring lipase activity and the method for simplifying production of a substrate solution for measuring lipase activity according to the present invention are used, the production of a substrate solution for measuring lipase activity in which DGGMR is included as a substrate for measuring lipase activity can be made simple, less time-consuming, and low-cost.

In addition, the process for producing a substrate solution for measuring lipase activity and the method for simplifying production of a substrate solution for measuring lipase activity according to the present invention do not necessitate cumbersome or special processing such that skill is required. Consequently, there is less possibility that the produced substrate solution for measuring lipase activity is a defective product that deviates from an established standard. Hence, the present invention makes it possible to provide medical institutions, etc., in a low-cost and reliable manner, with a substrate solution for measuring lipase activity in which accurate assay results (measured values) can be obtained.

BRIEF DESCRIPTION OF DRAWING

FIG. 1 is graphs each illustrating the correlation between measured values as obtained using a measuring reagent containing the substrate solution for measuring lipase activity produced by the process of present invention and measured values as obtained using a commercially available control reagent.

EMBODIMENTS FOR CARRYING OUT THE INVENTION

<1> Process for Producing Substrate Solution for Measuring Lipase Activity
1. Overview
(A) Outline Examples of a process for producing a substrate solution for measuring lipase activity according to the present invention include a process for producing a substrate solution that is used for measuring lipase activity in a sample and comprises, as a substrate for measuring lipase activity, 1,2-o-dilauryl-rac-glycero-3-glutaric acid (6'-methylresorufin) ester (DGGMR), the process comprising the steps of:

(1) mixing the substrate for measuring lipase activity and a side-chain-type nonreactive polyether-modified-type modified silicone oil or a polyoxyethylene/polyoxypropylene condensate to prepare a mixture; and (2) mixing all or a portion of the mixture of step (1) with water or an aqueous solution.

The process for producing a substrate solution for measuring lipase activity according to the present invention includes steps (1) and (2). Accordingly, the production process does not necessitate cumbersome or special processing such that skill is required, or does not necessitate a special apparatus, instruments, or other items. In this way, the production process can be used to produce a substrate solution for measuring lipase activity in which DGGMR is included as a substrate for measuring lipase activity.

(B) Embodiment in which Side-chain-type Nonreactive Polyether-modified-type Modified Silicone Oil is Used The process for producing a substrate solution for measuring lipase activity according to the present invention includes the following embodiment in which a side-chain-type nonreactive polyether-modified-type modified silicone oil is used.

"A process for producing a substrate solution that is used for measuring lipase activity in a sample and comprises, as a substrate for measuring lipase activity, 1,2-o-dilauryl-rac-glycero-3-glutaric acid (6'-methylresorufin) ester, the process comprising the steps of:

(1) mixing the substrate for measuring lipase activity and a side-chain-type nonreactive polyether-modified-type modified silicone oil to prepare a mixture; and (2) mixing all or a portion of the mixture of step (1) with water or an aqueous solution".

(C) Embodiment in which Polyoxyethylene/Polyoxypropylene Condensate is Used

According to the following embodiment of the present invention, the process for producing a substrate solution for measuring lipase activity includes use of a polyoxyethylene/polyoxypropylene condensate.

"A process for producing a substrate solution that is used for measuring lipase activity in a sample and comprises, as a substrate for measuring lipase activity, 1,2-o-dilauryl-rac-glycero-3-glutaric acid (6'-methylresorufin) ester, the process comprising the steps of:

(1) mixing the substrate for measuring lipase activity and a polyoxyethylene/polyoxypropylene condensate to prepare a mixture; and (2) mixing all or a portion of the mixture of step (1) with water or an aqueous solution".

2. Lipase

In the present invention, a lipase should have activity as a lipase, that is, should have lipase activity. The lipase is not particularly limited as long as the lipase has the lipase activity.

In the present invention, examples of the lipase include a pancreatic lipase (EC 3.1.1.3) that catalyzes a reaction in which ester bonds (at α-position (positions 1 and 3)) of a triglyceride (TG) (three long-chain fatty acids are each linked via an ester bond to glycerol) are hydrolyzed to produce two fatty acids and one β-monoglyceride.

The present invention is preferable for measuring the activity of a lipase present in body fluid, an organ, or a tissue, more preferable for measuring the activity of a lipase present in body fluid, still more preferable for measuring the activity of a lipase present in blood, serum, or plasma, and still more preferable for measuring the activity of a lipase present in serum or plasma.

In addition, the present invention is suitable for measuring the activity of a pancreatic lipase.

3. Sample

In the present invention, a sample for measuring lipase activity may be a sample that can contain the above lipase. The sample is not particularly limited as long as the sample can contain the above lipase.

Examples of the sample can include human samples and animal- or plant-derived samples.

Example of the human samples and the animal-derived samples can include, but are not limited to, human or animal body fluid (e.g., blood, serum, plasma, urine, semen, spinal fluid, saliva, sweat, teardrops, ascites, or amnion liquid); excrement (e.g., feces); organs (e.g., a pancreas, liver, or stomach); tissues (e.g., a hair, skin, nail, muscle, or nerve); and cells.

The present invention is suitable when the human- or animal-derived sample is used as a sample and more suitable when the human-derived sample is used as a sample.

In addition, the present invention is preferable when the body fluid, organ, or tissue is used as a sample, more preferable when the body fluid is used as a sample, still more preferable when the blood, serum, or plasma is used as a sample, and still more preferable when the serum or plasma is used as a sample.

Note that, in the present invention, a liquid sample is preferable. So, if the sample is not liquid, pretreatment (e.g., extraction or solubilization) may be performed in accordance with a known procedure to prepare a liquid sample.

In addition, the sample may be diluted or enriched as needed.

4. Substrate for Measuring Lipase Activity

In the present invention, a substrate that is used for measuring lipase activity contained in a sample (i.e., a substrate for measuring lipase activity) is 1,2-o-dilauryl-rac-glycero-3-glutaric acid (6'-methylresorufin) ester (DGGMR).

In the present invention, DGGMR, a substrate for measuring lipase activity, is made to contact a sample and make a reaction with a lipase contained in the sample. This lipase catalyzes hydrolysis to produce, from the DGGMR, 1,2-o-dilauryl-rac-glycerol and glutaric acid (6'-methylresorufin) ester.

This glutaric acid (6'-methylresorufin) ester is unstable and is thus hydrolyzed readily and naturally to give 6'-methylresorufin ($\lambda$max: 580 nm).

In the present invention, an increase in the resulting 6'-methylresorufin is measured by reading absorbance at or near 580 nm. Then, the activity value of the lipase contained in the sample can be determined.

Note that DGGMR is commercially available from, for example, Roche Diagnostics K. K. (Japan) or Sigma-Aldrich Co. LLC. (Japan).

5. Present Polymer (1) Overview

As described above, the process for producing a substrate solution for measuring lipase activity according to the present invention includes the steps of mixing the substrate (DGGMR) for measuring lipase activity and a side-chain-type nonreactive polyether-modified-type modified silicone oil or a polyoxyethylene/polyoxypropylene condensate (the present polymer) to prepare a mixture, and mixing all or a portion of this mixture with water or an aqueous solution.

(2) Side-chain-type Nonreactive Polyether-modified-type Modified Silicone Oil

The following describes a side-chain-type nonreactive polyether-modified-type modified silicone oil (hereinafter, sometimes referred to as "the present modified silicone oil") used in the present invention.

The silicone compound is a polymer containing, as a main chain, a siloxane linkage (—Si—O—Si—) and, as a side chain, an organic group (e.g., a methyl group ($CH_3$—)) bonded to a silicon atom.

Here, a linear silicone compound is called a silicone oil.

Note that the modified silicone oil is a compound in which an organic group is introduced into a portion of silicon atoms of a linear dimethyl silicone compound "$Si(CH_3)_3$—O—[$Si(CH_3)_2$—O—]m-$Si(CH_3)_3$".

Examples of this modified silicone oil include silicone oils in which various organic groups are introduced into part of side chains of polysiloxane, either end of polysiloxane, both ends of polysiloxane, or part of side chains and both ends of polysiloxane.

Among them, the silicone oil in which various organic groups are introduced into part of side chains of polysiloxane is a side-chain-type modified silicone oil "$Si(CH_3)_3$—O—[$Si(CH_3)_2$—O—]m-[$Si(CH_3)$(an organic group)-O—]n-$Si(CH_3)_3$".

Note that depending on characteristics of the organic groups introduced, the modified silicone oils are classified into a reactive silicone oil and a nonreactive silicone oil.

Depending on the organic group introduced, examples of the nonreactive modified silicone oil of the two include a polyether modified type, aralkyl modified type, fluoroalkyl modified type, long-chain alkyl modified type, higher fatty acid ester modified type, higher fatty acid amide modified type, polyether/long-chain alkyl/aralkyl modified type, long-chain alkyl/aralkyl modified type, and phenyl modified type silicone oil.

As the side-chain-type nonreactive modified silicone oil "$Si(CH_3)_3$—O—[$Si(CH_3)_2$—O-]m-[$Si(CH_3)$(an organic group)-O-]n-$Si(CH_3)_3$", examples of the modified type silicone oil include a polyether modified type silicone oil (the organic group: —$R(C_2H_4O)_a(C_3H_6O)_bR'$), a polyether/long-chain alkyl/aralkyl modified type silicone oil (the organic group: —$R(C_2H_4O)_a(C_3H_6O)_bR'$, —$C_aH_{2a+1}$, —$CH_2$—CH($CH_3$)—$C_6H_5$), an aralkyl modified type silicone oil (the organic group: —$CH_2$—CH($CH_3$)—$C_6H_5$), a fluoroalkyl modified type silicone oil (the organic group: —$CH_2CH_2CF_3$), a long-chain alkyl modified type silicone oil (the organic group: —$C_aH_{2a+1}$), a long-chain alkyl/aralkyl modified type silicone oil (the organic group: —$C_aH_{2a+1}$, —$CH_2$—CH($CH_3$)—$C_6H_5$), a higher fatty acid ester modified type silicone oil (the organic group: —OCOR), a higher fatty acid amide modified type silicone oil (the organic group: —RNHCOR'), and a phenyl modified type silicone oil (the organic group: —$C_6H_5$).

In the present invention, used is the side-chain-type nonreactive polyether-modified-type modified silicone oil "$Si(CH_3)_3$—O—[$Si(CH_3)_2$—O-]m-[$Si(CH_3)$(an organic group)-O-]n-$Si(CH_3)_3$" (the organic group: —$R(C_2H_4O)_a(C_3H_6O)_bR'$). (Alternatively, a polyoxyethylene/polyoxypropylene condensate is used.)

Example of this side-chain-type nonreactive polyether-modified-type modified silicone oil that is commercially available include "KF-351A", "KF-354L", "KF-355A", and "KF-6011" (the distributor for any of the above products is Shin-Etsu Chemical Co., Ltd. (Japan)).

(3) Polyoxyethylene/Polyoxypropylene Condensate

The following illustrates a polyoxyethylene/polyoxypropylene condensate (hereinafter, sometimes referred to as the "present POE/POP condensate") used in the present invention.

In the present invention, used is a polyoxyethylene/polyoxypropylene condensate "HO$(C_2H_4O)_a$—$(C_3H_6O)_b$—$(C_2H_4O)_c$H". (Alternatively, the side-chain-type nonreactive polyether-modified-type modified silicone oil is used.)

Examples of this polyoxyethylene/polyoxypropylene condensate (the present POE/POP condensate) include polyoxyethylene(16)polyoxypropylene(17)glycol (the quasi-medicine raw material standard name: polyoxyethylene polyoxypropylene glycol (16E.O.)(17P.O.)) and polyoxyethylene(20) polyoxypropylene(20)glycol (the quasi-medicine raw material standard name: polyoxyethylene polyoxypropylene glycol (20E.O.)(20P.O.)).

Examples of the present POE/POP condensate that is commercially available include polyoxyethylene(16)polyoxypropylene(17)glycol (the product name: "Pluronic L-34"; the distributor: ADEKA CORPORATION (Japan)) and polyoxyethylene(20)polyoxypropylene(20)glycol (the product name: "Pluronic L-44"; the distributor: ADEKA CORPORATION (Japan)).

6. Step of Mixing Substrate for Measuring Lipase Activity and Present Polymer to Prepare Mixture (1) Overview The process for producing a substrate solution for measuring lipase activity according to the present invention includes a step of mixing a substrate (DGGMR) for measuring lipase activity and a side-chain-type nonreactive polyether-modified-type modified silicone oil or a polyoxyethylene/polyoxypropylene condensate (the present polymer) to prepare a mixture.

Note that the substrate (DGGMR) for measuring lipase activity is as described in the section "4. Substrate for Measuring Lipase Activity".

Also, the "side-chain-type nonreactive polyether-modified-type modified silicone oil or the polyoxyethylene/polyoxypropylene condensate" (the present polymer) is as described in the section "5. Present Polymer".

(2) Mixing Substrate for Measuring Lipase Activity and Present Polymer

In the step of mixing a substrate for measuring lipase activity and the present polymer to prepare a mixture according to the present invention, the substrate for measuring lipase activity, namely, DGGMR is mixed with the present polymer.

That is, the substrate (DGGMR) for measuring lipase activity is directly mixed with the present polymer.

Conventionally, a surfactant used is first mixed with water or an aqueous solution, and the resulting mixture is then mixed with a substrate for measuring lipase activity.

The present invention, however, differs from such a conventional process, but provides a process comprising a step of directly mixing a substrate for measuring lipase activity, namely, DGGMR and the present polymer.

Note that as used herein, one kind of the present polymer may be mixed with the substrate for measuring lipase activity, or several kinds of the present polymer may be mixed with the substrate for measuring lipase activity.

(3) Mixed Amount of Substrate for Measuring Lipase Activity

In the step of mixing a substrate (DGGMR) for measuring lipase activity and the present polymer to prepare a mixture according to the present invention, the mixed amount of this substrate is not particularly limited.

Note that the concentration of the substrate (DGGMR) for measuring lipase activity according to the present invention is preferably 0.05 mM or higher after mixing with water or an aqueous solution (hereinafter, sometimes referred to as the "second mixing") in the "step of mixing all or a portion of the mixture of the substrate (DGGMR) for measuring lipase activity and the present polymer with water or an aqueous solution", for the purpose of producing an emulsified solution that contains a substrate for measuring lipase activity and is composed of stable and uniform micelle particles.

Note that after the second mixing, the preferable concentration of the substrate for measuring lipase activity is more preferably 0.1 mM or higher and still more preferably 0.2 mM or higher in view of the above purpose.

In addition, the concentration of the substrate for measuring lipase activity is preferably 2 mM or less after the second mixing in view of the above purpose.

Note that after the second mixing, the preferable concentration of the substrate for measuring lipase activity is more preferably 1 mM or less and still more preferably 0.8 mM or less in view of the above purpose.

The preferable concentration of the substrate (DGGMR) for measuring lipase activity according to the present invention after the second mixing is as described above.

In the "step of mixing a substrate (DGGMR) for measuring lipase activity and the present polymer to prepare a mixture" according to the present invention, the substrate for measuring lipase activity and the present polymer are mixed (hereinafter, sometimes referred to as the "first mixing"). At this time, the mixed amount of each of the substrate for measuring lipase activity and the present polymer may be considered and then determined such that the concentration of the substrate for measuring lipase activity after the second mixing is as described above. This is preferable in light of the production procedure.

Note that regarding the mixed amount and concentration of the substrate for measuring lipase activity, the following cases (a) and (b), for example, may be considered.

(a) Case where all of the Mixture of the Substrate for Measuring Lipase Activity and the Present Polymer is Mixed with Water or an Aqueous Solution The mixed amount of the substrate for measuring lipase activity mixed at the time of the first mixing is set to Ws (represented in grams). The final volume (e.g., a volume after filled to the mark) after water or an aqueous solution is mixed at the time of the second mixing is set to Vf (represented in mL). The molecular weight of the substrate for measuring lipase activity is set to MWs. In this case, the concentration Cs (represented in mM) of the substrate after the second mixing can be expressed in the following equation.

$$Cs=(Ws\times 10^6)/(Vf\times MWs).$$

Note that because the molecular weight MWs of the substrate (DGGMR) for measuring lipase activity is 752.05, the above equation can be expressed as follows.

$$Cs=(Ws\times 10^6)/(Vf\times 752.05).$$

Hence, in this case, the mixed amount Ws (represented in grams) of the substrate for measuring lipase activity mixed at the time of the first mixing can be expressed as follows.

$$Ws=(Cs\times Vf\times MWs)/10^6.$$

That is, $Ws=(Cs\times Vf\times 752.05)/10^6$.

(b) Case where a Portion of the Mixture of the Substrate for Measuring Lipase Activity and the Present Polymer is Mixed with Water or an Aqueous Solution The mixed amount of the substrate for measuring lipase activity mixed at the time of the first mixing is set to Ws (represented in grams). The final volume (e.g., a volume after filled to the mark) after water or an aqueous solution is mixed at the time of the second mixing is set to Vf (represented in mL). The molecular weight of the substrate for measuring lipase activity is set to MWs. Here, A % (by weight or by volume) of the mixture at the time of the first mixing is mixed with water or an aqueous solution at the time of the second mixing. In this case, the concentration Cs (represented in mM) of the substrate for measuring lipase activity after the second mixing can be expressed in the following equation.

$$Cs=(Ws\times 10^6)\times (A/100)/(Vf\times MWs)=(Ws\times A\times 10^4)/(Vf\times MWs).$$

Note that because the molecular weight MWs of the substrate (DGGMR) for measuring lipase activity is 752.05, the above equation can be expressed as follows.

$$Cs=(Ws\times A\times 10^4)/(Vf\times 752.05).$$

Hence, in this case, the mixed amount Ws (represented in grams) of the substrate for measuring lipase activity mixed at the time of the first mixing can be expressed as follows.

$$Ws=(Cs\times Vf\times MWs)/(A\times 10^4).$$

That is, $Ws=(Cs\times Vf\times 752.05)/(A\times 10^4)$.

(4) Mixed Amount of Present Polymer

In the step of mixing a substrate (DGGMR) for measuring lipase activity and the present polymer to prepare a mixture according to the present invention, the mixed amount of the present polymer is not particularly limited.

Note that the concentration of the present polymer is preferably 0.01% (w/v) or higher after the mixing with water or an aqueous solution (the "second mixing") in the "step of mixing all or a portion of the mixture of the substrate (DGGMR) for measuring lipase activity and the present polymer with water or an aqueous solution", for the purpose of producing an emulsified solution that contains a substrate for measuring lipase activity and is composed of stable and uniform micelle particles.

Note that after the second mixing, the preferable concentration of the present polymer is more preferably 0.05% (w/v) or higher and still more preferably 0.1% (w/v) or higher in view of the above purpose.

In addition, this concentration of the present polymer is preferably 20% (w/v) or less after the second mixing in view of the above purpose.

Note that after the second mixing, the preferable concentration of the present polymer is more preferably 10% (w/v) or less and still more preferably 5% (w/v) or less in view of the above purpose.

The preferable concentration of the present polymer after the second mixing is as described above.

In the "step of mixing a substrate (DGGMR) for measuring lipase activity and the present polymer to prepare a mixture" according to the present invention, the substrate for measuring lipase activity and the present polymer are mixed (the "first mixing"). At this time, the mixed amount of each of the substrate for measuring lipase activity and the present polymer may be considered and then determined such that the concentration of the present polymer after the second mixing is as described above. This is preferable in light of the production procedure.

Note that regarding the mixed amount and concentration of the present polymer, the following cases (a) and (b), for example, may be considered.

(a) Case where all of the Mixture of the Substrate for Measuring Lipase Activity and the Present Polymer is Mixed with Water or an Aqueous Solution The mixed amount of the present polymer mixed at the time of the first mixing is set to Wp (represented in grams). The final volume (e.g., a volume after filled to the mark) after water or an aqueous solution is mixed at the time of the second mixing is set to Vf (represented in mL). In this case, the concentration Cp (represented in % (w/v)) of the present polymer after the second mixing can be expressed as the following equation.

$$Cp=(Wp\times 100)/Vf.$$

Hence, in this case, the mixed amount Wp (represented in grams) of the present polymer mixed at the time of the first mixing can be expressed as follows.

$$Wp=(Cp\times Vf)/100.$$

(b) Case where a Portion of the Mixture of the Substrate for Measuring Lipase Activity and the Present Polymer is Mixed with Water or an Aqueous Solution The mixed amount of the present polymer mixed at the time of the first mixing is set to Wp (represented in grams). The final volume (e.g., a volume after filled to the mark) after water or an aqueous solution is mixed at the time of the second mixing is set to Vf (represented in mL). Here, A % (by weight or by volume) of the mixture at the time of the first mixing is mixed with water or an aqueous solution at the time of the second mixing. In this case, the concentration Cp (represented in % (w/v)) of the present polymer after the second mixing can be expressed as the following equation.

$$Cp=(Wp\times 100)\times (A/100)/Vf=(Wp\times A)/Vf.$$

Hence, in this case, the mixed amount Wp (represented in grams) of the present polymer mixed at the time of the first mixing can be expressed as follows.

$$Wp=(Cp\times Vf)/A.$$

(5) Mixing Procedure

In the step of mixing a substrate (DGGMR) for measuring lipase activity and the present polymer to prepare a mixture according to the present invention, the substrate for measuring lipase activity is mixed with the present polymer. This procedure is not particularly limited and any procedure can be adopted as long as the substrate for measuring lipase activity can be mixed with the present polymer.

Note that according to the present invention, the mixing may not be carried out in the following manners: a substrate for measuring lipase activity may be mixed into a solution containing an organic solvent (e.g., an alcohol); a liquid containing a substrate for measuring lipase activity is added dropwise and mixed into a solution; a liquid containing a substrate for measuring lipase activity is jet-injected into a solution; a substrate solution for measuring lipase activity is stirred using a strong mixer at a high speed; a substrate solution for measuring lipase activity is subjected to ultrasonication; or the like. Accordingly, the mixing does not necessitate cumbersome or special processing such that skill is required, or does not necessitate a special apparatus or other items. A common mixer may be used for the mixing at a typical speed. Likewise, a usual procedure may be used for the mixing. In this way, the mixture of the substrate for measuring lipase activity and the present polymer can be prepared.

(6) Mixing Temperature

In the step of mixing a substrate (DGGMR) for measuring lipase activity and the present polymer to prepare a mixture according to the present invention, the temperature when the substrate for measuring lipase activity is mixed with the present polymer is not particularly limited. However, this step is carried out preferably at a temperature near the clouding point of the present polymer used or at the clouding point or lower, for the purpose of producing an emulsified solution that contains a substrate for measuring lipase activity and is composed of stable and uniform micelle particles.

Note that a clouding point is a temperature at which micelles of a nonionic surfactant, etc., cannot be formed when the temperature of an aqueous solution containing the surfactant is increased. The clouding point is also a temperature at which that aqueous solution becomes clouded. Different surfactants have different clouding points.

As used herein, the temperature at or near the clouding point of the present polymer means a temperature range including the clouding point of the present polymer ±25° C.

The temperature at or near the clouding point of the present polymer is preferably a temperature range including the clouding point of the present polymer ±15° C., more preferably a temperature range including the clouding point of the present polymer ±10° C., and still more preferably a temperature range including the clouding point of the present polymer ±5° C.

In the present invention, the step of mixing a substrate for measuring lipase activity and the present polymer to prepare a mixture is preferably carried out at a temperature near the clouding point of the present polymer or lower.

Note that for example, KF-351A, one of the present modified silicone oils, has a clouding point of 52° C. (a self-measured value); KF-355A has a clouding point of 67° C. (a self-measured value); and KF-6011 has a clouding point of 64° C. (a self-measured value).

Note that KF-354L did not reach a clouding point even at 77° C., which is the upper limit of the preset temperature of a thermostat water bath used for measuring the clouding point, so that the clouding point exceeds 77° C.

In addition, Pluronic L-34, one of the present POE/POP condensates, for example, has a clouding point of 65° C. (a self-measured value); and Pluronic L-44 has a clouding point of 67° C. (a self-measured value).

In view of the above purpose, the step of mixing a substrate for measuring lipase activity and the present polymer to prepare a mixture is carried out preferably at the clouding point of the present polymer used ±25° C. or a temperature lower than this range, more preferably at the clouding point of the present polymer used ±15° C. or a temperature lower than this range, still more preferably at the clouding point of the present polymer used ±10° C. or a temperature lower than this range, and still more preferably at the clouding point of the present polymer used ±5° C. or a temperature lower than this range.

In addition, in the step of mixing a substrate for measuring lipase activity and the present polymer to prepare a mixture according to the present invention, the substrate for measuring lipase activity is mixed with the present polymer. Regarding the temperature at this time, the step is carried out at preferably a temperature equal to or higher than the melting point of each of the substrate (DGGMR) for measuring lipase activity and the present polymer used, for the purpose of producing an emulsified solution that contains a substrate for measuring lipase activity and is composed of stable and uniform micelle particles.

In view of the above purpose, the step of mixing a substrate for measuring lipase activity and the present polymer to prepare a mixture is carried out preferably at 2° C. or higher, more preferably at 5° C. or higher, and still more preferably at 10° C. or higher.

(7) Mixing Duration

In the step of mixing a substrate (DGGMR) for measuring lipase activity and the present polymer to prepare a mixture according to the present invention, the substrate for measuring lipase activity is mixed with the present polymer. The duration is not particularly limited as long as the substrate for measuring lipase activity can be uniformly mixed with the present polymer.

Usually, 5 minutes or longer of the mixing is preferable for the purpose of producing an emulsified solution that contains a substrate for measuring lipase activity and is composed of stable and uniform micelle particles. Note that 5 minutes is usually sufficient.

In addition, the duration required for the mixing of the substrate for measuring lipase activity and the present polymer does not have a particular upper limit. For example, the mixing may be carried out for several hours. In light of the idea that time is cost, the duration may be usually within 10 minutes even if the mixing is performed with care.

7. Step of Mixing Water or Aqueous Solution with Mixture of Substrate for Measuring Lipase Activity and Present Polymer (1) Overview The process for producing a substrate solution for measuring lipase activity according to the present invention includes a step of mixing water or an aqueous solution with all or a portion of the resulting mixture prepared in the "step of mixing a substrate (DGGMR) for measuring lipase activity and a side-chain-type nonreactive polyether-modified-type modified silicone oil or a polyoxyethylene/polyoxypropylene condensate (the present polymer) to prepare a mixture".

Note that the substrate for measuring lipase activity is as described in the section "4. Substrate for Measuring Lipase Activity".

Also, the present polymer is as described in the section "5. Present Polymer".

Also, the step of mixing a substrate for measuring lipase activity and the present polymer to prepare a mixture is as described in the section "6. Step of Mixing Substrate for Measuring Lipase Activity and Present Polymer to Prepare Mixture".

(2) Water or Aqueous Solution

In the step of mixing water or an aqueous solution with all or a portion of the resulting mixture prepared by mixing the substrate for measuring lipase activity and the present polymer to prepare a mixture of interest according to the present invention, the water or aqueous solution is not particularly limited.

Examples of the water can include, but are not particularly limited to, pure water, distilled water, and purified water.

In addition, this aqueous solution is not particularly limited as long as water is used as a solvent. Examples can include aqueous solutions containing at least one selected from the group consisting of a lipase promoter, lipase activator, colipase, and buffer.

(a) Lipase Promoter

In the present invention, the lipase promoter that can be included in the above aqueous solution may be a substance that can promote lipase activity. Examples can include, but are not particularly limited to, bile acid and a salt thereof Examples of the bile acid can include deoxycholic acid, taurodeoxycholic acid, glycodeoxycholic acid, cholic acid, lithocholic acid, glycocholic acid, taurocholic acid, chenodeoxycholic acid, ursodeoxycholic acid, 7-oxolithocholic acid, 12-oxolithocholic acid, 12-oxochenodeoxycholic acid, 7-oxodeoxycholic acid, hyocholic acid, hyodeoxycholic acid, dehydrocholic acid, and cholic acid derivatives.

In addition, examples of a salt of the bile acid include alkali metal or alkaline-earth metal salts of bile acid and an ammonium salt of bile acid.

Examples of the alkali metal can include potassium, sodium and lithium. In addition, examples of the alkaline-earth metal can include magnesium and calcium.

In the present invention, bile acid or a salt thereof is preferable as the lipase promoter because of their lipase activity-promoting function, an ability to form an interface composed of a substrate for measuring lipase activity, water solubility, and cost.

As the bile acid, taurodeoxycholic acid is preferable because it is miscible in an acidic range at which a substrate for measuring lipase activity is stable. Also, in view of cost, deoxycholic acid is preferable.

As the bile acid, more preferred is taurodeoxycholic acid.

As a salt of the bile acid, an alkali metal salt of the bile acid is preferable, a potassium or sodium salt of the bile acid is more preferable, and a sodium salt of the bile acid is still more preferable.

Thus, as a salt of the bile acid, an alkali metal (e.g., potassium or sodium) salt of deoxycholic acid or taurodeoxycholic acid is preferable, an alkali metal (e.g., potassium or sodium) salt of taurodeoxycholic acid is more preferable, and a sodium salt of taurodeoxycholic acid is still more preferable.

Note that the concentration of the lipase promoter according to the present invention is preferably 0.2% (w/v) or higher after "water or an aqueous solution is mixed (the second mixing) with all or a portion of the mixture prepared by mixing the substrate for measuring lipase activity and the present polymer".

Note that after the second mixing, the concentration of the lipase promoter is more preferably 0.4% (w/v) or higher and still more preferably 1% (w/v) or higher.

In addition, the concentration of the lipase promoter is preferably 20% (w/v) or less after the second mixing.

Note that after the second mixing, the preferable concentration of the lipase promoter is more preferably 10% (w/v) or less and still more preferably 5% (w/v) or less.

The preferable concentration of the lipase promoter after the second mixing according to the present invention is as described above.

In the present invention, the mixed ratio of the "mixture of the substrate for measuring lipase activity and the present polymer" to the above aqueous solution is considered such that the concentration of the lipase promoter after the second mixing fits the above concentration. Based on the above, it is preferable to include a suitable concentration of the lipase promoter into the corresponding aqueous solution.

(b) Lipase Activator

In the present invention, the lipase activator that can be included in the above aqueous solution may be a substance that can activate a lipase. Examples can include, but are not particularly limited to, an ion or salt of an alkaline-earth metal.

Examples of the ion or salt of an alkaline-earth metal can include a beryllium ion or beryllium salt, a magnesium ion or magnesium salt, and a calcium ion or calcium salt.

Examples of the calcium salt can include a water-soluble calcium salt. Specific examples can include a water-soluble salt containing a monovalent or divalent or higher anion and a calcium ion.

Note that examples of the anion can include a halogen ion, an acid group of an organic compound, and an acid group of an inorganic compound.

Examples of the halogen ion can include a fluorine ion and a chlorine ion.

Examples of the acid group of an organic compound can include an acetate ion, citrate ion and gluconate ion.

Examples of the acid group of an inorganic compound can include a sulfate ion, phosphate ion, and carbonate ion.

The lipase activator according to the present invention is preferably an ion or salt of an alkaline-earth metal.

Note that as the ion or salt of an alkaline-earth metal, a calcium ion or a calcium salt is preferable in view of the following points (i) and (ii):

(i) ability to activate a lipase; and (ii) a fatty acid that is released from a substrate for measuring lipase activity while the lipase exerts its catalytic activity disrupts an interface composed of the substrate for measuring lipase activity, but a calcium ion or a calcium salt can capture the free fatty acid, thereby preventing the interface from being disrupted.

Here, preferred is a water-soluble calcium salt containing an anion and a calcium ion.

Examples of a preferable anion include a halogen ion and an acid group of an organic compound. Specifically, more preferred is a chlorine ion or an acetate ion.

Thus, as the calcium salt, preferred is a calcium halide or a calcium salt of an acid group of an organic compound. Specifically, more preferred is calcium chloride or calcium acetate.

Note that the concentration of the lipase activator according to the present invention is preferably 0.1 mM or higher after "water or an aqueous solution is mixed (the second mixing) with all or a portion of the mixture prepared by mixing the substrate for measuring lipase activity and the present polymer".

Note that after the second mixing, the preferable concentration of the lipase activator is more preferably 1 mM or higher and still more preferably 5 mM or higher.

In addition, this concentration of the lipase activator is preferably 100 mM or less after the second mixing.

Note that after the second mixing, the preferable concentration of the lipase activator is more preferably 50 mM or less and still more preferably 25 mM or less.

The preferable concentration of the lipase activator after the second mixing according to the present invention is as described above.

In the present invention, the mixed ratio of the "mixture of the substrate for measuring lipase activity and the present polymer" to the above aqueous solution is considered such that the concentration of the lipase activator after the second mixing fits the above concentration. Based on the above, it is preferable to include a suitable concentration of the lipase activator into the corresponding aqueous solution.

(c) Colipase

In the present invention, the colipase that can be included in an aqueous solution may have the effect, function, or activity of a colipase. Examples can include, but are not particularly limited to, colipases derived from mammals (e.g., a human, pig) and colipases prepared, modified, or altered using genetic engineering.

In the present invention, preferred is a colipase derived from a mammal (e.g., a pig). More preferred is a colipase derived from the pancreas of a mammal (e.g., a pig).

Note that the activity value of the colipase according to the present invention is preferably 15K Unit/L or higher after "water or an aqueous solution is mixed (the second mixing) with all or a portion of the mixture prepared by mixing the substrate for measuring lipase activity and the present polymer".

Note that after the second mixing, the preferable activity value of the colipase is more preferably 150K Unit/L or higher and still more preferably 750K Unit/L or higher.

In addition, the activity value of the colipase is preferably 7,500K Unit/L or less after the second mixing.

Note that after the second mixing, the activity value of the colipase is more preferably 3,750K Unit/L or less and still more preferably 2,250K Unit/L or less.

The preferable activity value of the colipase after the second mixing according to the present invention is as described above.

In the present invention, the mixed ratio of the "mixture of the substrate for measuring lipase activity and the present polymer" to the above aqueous solution is considered such that the activity value of the colipase after the second mixing fits the above activity value. Based on the above, it is preferable that the above aqueous solution contains the colipase with suitable activity value.

Note that each activity value (Unit/L) of the colipase is based on how the activity value of a pig pancreatic colipase (Roche Diagnostics K. K. (Japan)) is designated (1 mg/L=75K Unit/L).

Note that the colipase is commercially available from, for example, Roche Diagnostics K. K. (Japan) or Sigma-Aldrich Co. LLC. (Japan).

(d) pH

The substrate (DGGMR) for measuring lipase activity according to the present invention is stable at or near pH 4.

Thus, the pH is preferably a pH within a certain range relative to pH 4 after "water or an aqueous solution is mixed (the second mixing) with all or a portion of the mixture prepared by mixing the substrate for measuring lipase activity and the present polymer".

Specifically, in view of stability of the substrate (DGGMR) for measuring lipase activity, the pH after the second mixing is preferably from 2 to 7, more preferably from 3 to 5, and still more preferably from 3.5 to 4.5 (any of the pH values is a value at 20° C.).

The pH after the second mixing according to the present invention is as described above.

In the present invention, it is preferable to set the pH of the above aqueous solution to a suitable pH such that the pH after the second mixing fits the above-described pH.

(e) Buffer

In the present invention, water or an aqueous solution is mixed (the second mixing) with all or a portion of the mixture prepared by mixing the substrate for measuring lipase activity and the present polymer. Then, to keep the pH within the pH range described in (d), the aqueous solution may contain, as needed, a buffer with buffering capability within the above pH range.

Examples of the buffer that can be included in the above aqueous solution according to the present invention can include, but are not particularly limited to, organic acids (e.g., tartaric acid, succinic acid, malonic acid, citric acid); glycine; phosphoric acid; and salts thereof.

In the present invention, the concentration of the buffer in this buffer-containing aqueous solution (i.e., a buffer solution) is not particularly limited as long as the buffering capability can be exerted within a prescribed pH range.

For example, after the second mixing, the concentration of the buffer is preferably 5 mM or higher, more preferably 10 mM or higher, and still more preferably 30 mM or higher.

In addition, after the second mixing, the concentration of the buffer is preferably 500 mM or less, more preferably 100 mM or less, and still more preferably 50 mM or less.

The preferable concentration of the buffer after the second mixing according to the present invention is as described above.

In the present invention, it is preferable that the above aqueous solution contains a suitable concentration of the buffer such that the concentration of the buffer after the second mixing fits the above-described concentration.

(3) Mixing Water or Aqueous Solution with Mixture of Substrate for Measuring Lipase Activity and Present Polymer In the step of mixing water or an aqueous solution with all or a portion of the mixture prepared by mixing the substrate for measuring lipase activity and the present polymer according to the present invention, all or a portion of the mixture is mixed with water or an aqueous solution.

Conventionally, a surfactant used is first mixed with water or an aqueous solution, and the resulting mixture is then mixed with a substrate for measuring lipase activity.

The present invention, however, differs from such a conventional process, but provides a process comprising the steps of directly mixing a substrate for measuring lipase activity and the present polymer; and mixing water or an aqueous solution with all or a portion of the resulting mixture of the substrate for measuring lipase activity and the present polymer as so prepared.

Meanwhile, the step of mixing water or an aqueous solution with all or a portion of the mixture prepared by mixing the substrate for measuring lipase activity and the present polymer according to the present invention is not particularly limited. For example, all or a portion of "the mixture prepared by mixing the substrate for measuring lipase activity and the present polymer" may be added to and mixed with "water or an aqueous solution". In addition, "water or an aqueous solution" may be added to or mixed with all or a portion of "the mixture prepared by mixing the substrate for measuring lipase activity and the present polymer". Also, other embodiments are acceptable.

Note that, in the present invention, the mixed ratio of the mixture of the substrate for measuring lipase activity and the present polymer to the water or aqueous solution is not particularly limited and may be appropriately determined.

Note that mixing the mixture of the substrate for measuring lipase activity and the present polymer with the water or aqueous solution may be considered in view of the following aspects (i) and (ii).

(i) In View of Concentration of Substrate for Measuring Lipase Activity

As described in detail in the above section 6.(3), the concentration of the substrate for measuring lipase activity after the second mixing is preferably 0.05 mM or higher, more preferably 0.1 mM or higher, and still more preferably 0.2 mM or higher in view of the above purpose.

As also described in detail in the above section 6.(3), the concentration of the substrate for measuring lipase activity after the second mixing is preferably 2 mM or less, more preferably 1 mM or less, and still more preferably 0.8 mM or less in view of the above purpose.

Note that regarding the relationship between the preferable concentration of the substrate for measuring lipase activity and the final volume after water or an aqueous solution is mixed at the time of the second mixing, the following cases (a) and (b), for example, may be considered.

(a) Case where all of the Mixture of the Substrate for Measuring Lipase Activity and the Present Polymer is Mixed with Water or an Aqueous Solution The mixed amount of the substrate for measuring lipase activity mixed at the time of the first mixing is set to Ws (represented in grams). The final volume (e.g., a volume after filled to the mark) after water or an aqueous solution is mixed at the time of the second mixing is set to Vf (represented in mL). The molecular weight of the substrate for measuring lipase activity is set to MWs. In this case, the concentration Cs (represented in mM) of the substrate for measuring lipase activity after the second mixing can be expressed in the following equation.

$$Cs=(Ws \times 10^6)/(Vf \times MWs).$$

Note that because the molecular weight MWs of the substrate (DGGMR) for measuring lipase activity is 752.05, the above equation can be expressed as follows.

$$Cs=(Ws \times 10^6)/(Vf \times 752.05).$$

Thus, in this case, the final volume Vf (represented in mL) after water or an aqueous solution is mixed at the time of the second mixing can be expressed as follows.

$$Vf=(Ws \times 10^6)/(Cs \times MWs).$$

That is, Vf=(Ws×10⁶)/(Cs×752.05).

Accordingly, at the time of the second mixing, water or an aqueous solution may be mixed so as to achieve the volume Vf (represented in mL) calculated using the above equation. This enables a substrate solution for measuring lipase activity to contain a desired concentration of the substrate (DGGMR) for measuring lipase activity.

(b) Case where a Portion of the Mixture of the Substrate for Measuring Lipase Activity and the Present Polymer is Mixed with Water or an Aqueous Solution The mixed amount of the substrate for measuring lipase activity mixed at the time of the first mixing is set to Ws (represented in grams). The final volume (e.g., a volume after filled to the mark) after water or an aqueous solution is mixed at the time of the second mixing is set to Vf (represented in mL). The molecular weight of the substrate for measuring lipase activity is set to MWs. Here, A % (by weight or by volume) of the mixture at the time of the first mixing is mixed with water or an aqueous solution at the time of the second mixing. In this case, the concentration Cs (represented in mM) of the substrate for measuring lipase activity after the second mixing can be expressed in the following equation.

$$Cs=(Ws \times 10^6) \times (A/100)/(Vf \times MWs)=(Ws \times A \times 10^4)/(Vf \times MWs).$$

Note that because the molecular weight MWs of the substrate (DGGMR) for measuring lipase activity is 752.05, the above equation can be expressed as follows.

$$Cs=(Ws \times A \times 10^4)/(Vf \times 752.05).$$

Thus, in this case, the final volume Vf (represented in mL) after water or an aqueous solution is mixed at the time of the second mixing can be expressed as follows.

$$Vf=(Ws \times A \times 10^4)/(Cs \times MWs).$$

That is, Vf=(Ws×A×10⁴)/(Cs×752.05).

Accordingly, at the time of the second mixing, water or an aqueous solution may be mixed so as to achieve the volume Vf (represented in mL) calculated using the above equation. This enables a substrate solution for measuring lipase activity to contain a desired concentration of the substrate (DGGMR) for measuring lipase activity.

(ii) In View of Concentration of Present Polymer

As described in detail in the above section 6.(4), the preferable concentration of the present polymer after the second mixing is preferably 0.01% (w/v) or higher, more preferably 0.05% (w/v) or higher, and still more preferably 0.1% (w/v) or higher in view of the above purpose.

As also described in detail in the above section 6.(4), the preferable concentration of the present polymer after the second mixing is preferably 20% (w/v) or less, more preferably 10% (w/v) or less, and still more preferably 5% (w/v) or less in view of the above purpose.

Regarding the relationship between the preferable concentration of the present polymer and the final volume after water or an aqueous solution is mixed at the time of the second mixing, the following cases (a) and (b), for example, may be considered.

(a) Case where all of the Mixture of the Substrate for Measuring Lipase Activity and the Present Polymer is Mixed with Water or an Aqueous Solution The mixed amount of the present polymer mixed at the time of the first mixing is set to Wp (represented in grams). The final volume (e.g., a volume after filled to the mark) after water or an aqueous solution is mixed at the time of the second mixing is set to Vf (represented in mL). In this case, the concentration Cp (represented in % (w/v)) of the present polymer after the second mixing can be expressed as the following equation.

$$Cp=(Wp \times 100)/Vf.$$

Thus, in this case, the final volume Vf (represented in mL) after water or an aqueous solution is mixed at the time of the second mixing can be expressed as follows.

$$Vf=(Wp \times 100)/Cp.$$

Accordingly, at the time of the second mixing, water or an aqueous solution may be mixed so as to achieve the volume Vf (represented in mL) calculated using the above equation. This enables a substrate solution for measuring lipase activity to contain a desired concentration of the present polymer.

(b) Case where a Portion of the Mixture of the Substrate for Measuring Lipase Activity and the Present Polymer is Mixed with Water or an Aqueous Solution The mixed amount of the present polymer mixed at the time of the first mixing is set to Wp (represented in grams). The final volume (e.g., a volume after filled to the mark) after water or an aqueous solution is mixed at the time of the second mixing is set to Vf (represented in mL). Here, A % (by weight or by volume) of the mixture at the time of the first mixing is mixed with water or an aqueous solution at the time of the second mixing. In this case, the concentration Cp (represented in % (w/v)) of the present polymer after the second mixing can be expressed as the following equation.

$$Cp = (Wp \times 100) \times (A/100)/Vf = (Wp \times A)/Vf.$$

Thus, in this case, the final volume Vf (represented in mL) after water or an aqueous solution is mixed at the time of the second mixing can be expressed as follows.

$$Vf = (Wp \times A)/Cp.$$

Accordingly, at the time of the second mixing, water or an aqueous solution may be mixed so as to achieve the volume Vf (represented in mL) calculated using the above equation. This enables a substrate solution for measuring lipase activity to contain a desired concentration of the present polymer.

Note that the step of mixing water or an aqueous solution with all or a portion of the mixture prepared by mixing the substrate for measuring lipase activity and the present polymer according to the present invention may be carried out using two or more stages (steps).

Note that this step may be carried out using multiple stages (steps) in such a manner. This is preferable for the purpose of producing an emulsified solution that contains a substrate for measuring lipase activity and is composed of stable and uniform micelle particles.

Regarding the procedure in which this step is carried out using multiple stages, this procedure is feasible as long as this step is carried out using multiple stage. Examples can include, but are not particularly limited to, procedures using the following stages <A> and <B>.

Stage <A> in which a certain quantity of water or an aqueous solution is mixed with all or a portion of the mixture prepared by mixing the substrate for measuring lipase activity and the present polymer.

Stage <B> in which an additional certain quantity of water or an aqueous solution is mixed with the mixed liquid after the above water or aqueous solution is mixed with the mixture (the mixture of the substrate for measuring lipase activity and the present polymer) at the stage <A>.

Note that in this case, Va (represented in mL) is set to the volume (fixed volume) of the "water or aqueous solution" mixed with "all or a portion of the mixture prepared by mixing the substrate for measuring lipase activity and the present polymer" at the stage <A>. Vf (represented in mL) is set to the final volume (e.g., a volume after filled to the mark) after "an additional certain quantity of water or an aqueous solution" is mixed with the mixed liquid at the stage <B> (i.e., the final volume after water or an aqueous solution is mixed at the time of the second mixing). For the purpose of producing an emulsified solution that contains a substrate for measuring lipase activity and is composed of stable and uniform micelle particles, the ratio (Vf/Va) calculated by Vf divided by Va is preferably from 1 to 500.

That is, in view of the above purpose, it is preferable that the above Va and Vf values (volumes) are selected such that the ratio (Vf/Va) calculated by Vf divided by Va is within a range from 1 to 500.

Likewise, in view of the above purpose, the ratio (Vf/Va) calculated by Vf divided by Va is more preferably from 2 to 200 and still more preferably from 5 to 100.

That is, in view of the above purpose, it is more preferable that the above Va and Vf values (volumes) are selected such that the ratio (Vf/Va) calculated by Vf divided by Va is within a range from 2 to 200. It is still more preferable that the above Va and Vf values (volumes) are selected such that the ratio (Vf/Va) is within a range from 5 to 100.

Note that there is no limitation regarding the stage <A> "in which a certain quantity of water or an aqueous solution is mixed with all or a portion of the mixture prepared by mixing the substrate for measuring lipase activity and the present polymer". For example, all or a portion of "the mixture prepared by mixing the substrate for measuring lipase activity and the present polymer" may be added to and mixed with a certain quantity of "water or an aqueous solution". In addition, a certain quantity of "water or an aqueous solution" may be added to and mixed with all or a portion of "the mixture prepared by mixing the substrate for measuring lipase activity and the present polymer". Also, other embodiments are acceptable.

In addition, there is no limitation regarding the stage <B> "in which an additional certain quantity of water or an aqueous solution is mixed with the mixed liquid after the above water or aqueous solution is mixed with the mixture (the mixture of the substrate for measuring lipase activity and the present polymer) at the stage <A>". For example, the "mixed liquid after the above water or aqueous solution is mixed with the mixture (the mixture of the substrate for measuring lipase activity and the present polymer) at the stage <A>" may be added to and mixed with a certain quantity of "water or an aqueous solution". In addition, a certain quantity of "water or an aqueous solution" may be added to and mixed with the "mixed liquid after the above water or aqueous solution is mixed with the mixture (the mixture of the substrate for measuring lipase activity and the present polymer) at the stage <A>". Also, other embodiments are acceptable.

(4) Mixing Procedure

In the step of mixing water or an aqueous solution with all or a portion of the mixture prepared by mixing the substrate for measuring lipase activity and the present polymer according to the present invention, all or a portion of the mixture is mixed with water or an aqueous solution. This procedure is not particularly limited and any procedure can be adopted as long as the mixture can be mixed with the water or aqueous solution.

Note that the mixing according to the present invention may be performed such that: a substrate for measuring lipase activity may be mixed into a solution containing an organic solvent (e.g., an alcohol); a liquid containing a substrate for measuring lipase activity is added dropwise and mixed into a solution; a liquid containing a substrate for measuring lipase activity is jet-injected into a solution; a substrate solution for measuring lipase activity is stirred using a strong mixer at a high speed; a substrate solution for measuring lipase activity is subjected to ultrasonication; or the like. Accordingly, the mixing does not necessitate cumbersome or special processing such that skill is required, or does not necessitate a special apparatus or other items. A common mixer may be used for the stirring at a typical speed. Likewise, a usual procedure may be used for the mixing. In this way, all or a portion of the mixture of the substrate for measuring lipase activity and the present polymer can be mixed with water or an aqueous solution.

(5) Mixing Temperature

In the step of mixing water or an aqueous solution with all or a portion of the mixture prepared by mixing the substrate for measuring lipase activity and the present polymer according to the present invention, all or a portion of the mixture is mixed with water or an aqueous solution. At this time, the temperature is not particularly limited, and the step may be carried out at a temperature equal to or lower than the clouding point of the present polymer used. This temperature is preferable for the purpose of producing an emulsified solution that contains a substrate for measuring lipase activity and is composed of stable and uniform micelle particles.

Meanwhile, the step of mixing water or an aqueous solution with all or a portion of the mixture prepared by mixing the substrate for measuring lipase activity and the present polymer is carried out more preferably at a temperature equal to or lower than the temperature that is lower by 10° C. than the clouding point of the present polymer used and still more preferably at 25° C. or lower in view of the above purpose.

In addition, in the step of mixing water or an aqueous solution with all or a portion of the mixture prepared by mixing the substrate for measuring lipase activity and the present polymer according to the present invention, all or a portion of the mixture of the substrate for measuring lipase activity and the present polymer is mixed with water or an aqueous solution. Regarding the temperature at this time, this step is preferably carried out at a temperature equal to or higher than the melting point of each of the substrate (DGGMR) for measuring lipase activity, the present polymer used, and the water or aqueous solution used. This temperature is preferable for the purpose of producing an emulsified solution that contains a substrate for measuring lipase activity and is composed of stable and uniform micelle particles.

Here, the step of mixing water or an aqueous solution with all or a portion of the mixture prepared by mixing the substrate for measuring lipase activity and the present polymer is carried out more preferably at 10° C. or higher and still more preferably at 15° C. or higher in view of the above purpose.

(6) Mixing Duration

In the step of mixing water or an aqueous solution with all or a portion of the mixture prepared by mixing the substrate for measuring lipase activity and the present polymer according to the present invention, all or a portion of the mixture is mixed with water or an aqueous solution. This duration is not particularly limited as long as the mixture of the substrate for measuring lipase activity and the present polymer can be uniformly mixed with the water or aqueous solution.

Usually, 5 minutes or longer of the mixing is preferable for the purpose of producing an emulsified solution that contains a substrate for measuring lipase activity and is composed of stable and uniform micelle particles. Note that 5 minutes is usually sufficient.

In addition, the duration required for mixing the mixture of the substrate for measuring lipase activity and the present polymer with water or an aqueous solution does not have a particular upper limit. For example, the mixing may be carried out for several hours. In light of the idea that time is cost, the duration may be usually within 10 minutes even if the mixing is performed with care.

8. Diameter of Micelles in Emulsion of Substrate Solution for Measuring Lipase Activity As described previously, a lipase acts most effectively in a water-oil interface of an emulsified triglyceride substrate. The reaction rate of the lipase involves the surface area of the substrate dispersed. Thus, for measuring the lipase activity, it seems critical to prepare a substrate composed of stable and uniform micelle particles (see Non Patent Document 2).

In the solution containing a substrate (DGGMR) for measuring lipase activity according to the present invention, when the diameter (particle size) of micelles in an emulsion thereof is be within a range from 60 to 1,500 nm, the reaction rate of the lipase is high, and also, the emulsion is stable. Accordingly, this substrate solution for measuring lipase activity can be stored and used for a long period and is thus preferable.

Because of this, in the substrate solution for measuring lipase activity according to the present invention, micelles in the emulsion have a diameter (particle size) of more preferably from 70 to 1,000 nm, still more preferably from 80 to 600 nm, and still more preferably from 100 to 200 nm.

<2> Method for Simplifying Production of Substrate Solution for Measuring Lipase Activity 1. Overview (A) Outline A method for simplifying production of a substrate solution that is used for measuring lipase activity in a sample and comprises, as a substrate for measuring lipase activity, 1,2-o-dilauryl-rac-glycero-3-glutaric acid (6'-methylresorufin) ester (DGGMR) according to the present invention, comprises the steps of:

(1) mixing the substrate for measuring lipase activity and a side-chain-type nonreactive polyether-modified-type modified silicone oil or a polyoxyethylene/polyoxypropylene condensate (the present polymer) to prepare a mixture; and (2) mixing all or a portion of the mixture of step (1) with water or an aqueous solution.

Here, the method for simplifying production of a substrate solution for measuring lipase activity according to the present invention includes steps (1) and (2), and thus does not necessitate cumbersome or special processing such that skill is required, or does not necessitate a special apparatus, instruments, or other items. Hence, the method can simplify the production of a substrate solution for measuring lipase activity in which DGGMR is included as a substrate for measuring lipase activity.

(B) Embodiment in which Side-chain-type Nonreactive Polyether-modified-type Modified Silicone Oil is Used.

According to the following embodiment of the present invention, the method for simplifying production of a substrate solution for measuring lipase activity includes use of a side-chain-type nonreactive polyether-modified-type modified silicone oil.

"A method for simplifying production of a substrate solution that is used for measuring lipase activity in a sample and comprises, as a substrate for measuring lipase activity, 1,2-o-dilauryl-rac-glycero-3-glutaric acid (6'-methylresorufin) ester, the method comprising the steps of:

(1) mixing the substrate for measuring lipase activity and a side-chain-type nonreactive polyether-modified-type modified silicone oil to prepare a mixture; and (2) mixing all or a portion of the mixture of step (1) with water or an aqueous solution".

(C) Embodiment in which Polyoxyethylene/Polyoxypropylene Condensate is Used.

According to the following embodiment of the present invention, the method for simplifying production of a substrate solution for measuring lipase activity includes use of a polyoxyethylene/polyoxypropylene condensate.

"A method for simplifying production of a substrate solution that is used for measuring lipase activity in a sample and comprises, as a substrate for measuring lipase activity, 1,2-o-dilauryl-rac-glycero-3-glutaric acid (6'-methylresorufin) ester, the method comprising the steps of:

(1) mixing the substrate for measuring lipase activity and a polyoxyethylene/polyoxypropylene condensate to prepare a mixture; and (2) mixing all or a portion of the mixture of step (1) with water or an aqueous solution".

2. Lipase

The lipase in the method for simplifying production of a substrate solution for measuring lipase activity according to the present invention is as described in the chapter <1>, the section "2. Lipase".

3. Sample

The sample in the method for simplifying production of a substrate solution for measuring lipase activity according to the present invention is as described in the chapter <1>, the section "3. Sample".

4. Substrate for Measuring Lipase Activity

The substrate for measuring lipase activity in the method for simplifying production of a substrate solution for measuring lipase activity according to the present invention is as described in the chapter <1>, the section "4. Substrate for Measuring Lipase Activity".

5. Present Polymer

The "side-chain-type nonreactive polyether-modified-type modified silicone oil or the polyoxyethylene/polyoxypropylene condensate" (the present polymer) in the method for simplifying production of a substrate solution for measuring lipase activity according to the present invention is as described in the chapter <1>, the section "5. Present Polymer".

6. Step of Mixing Substrate for Measuring Lipase Activity and Present Polymer to Prepare Mixture The step of mixing a substrate for measuring lipase activity and the present polymer to prepare a mixture in the method for simplifying production of a substrate solution for measuring lipase activity according to the present invention is as described in the chapter <1>, the section "6. Step of Mixing Substrate for Measuring Lipase Activity and Present Polymer to Prepare Mixture".

7. Step of Mixing Water or Aqueous Solution with Mixture of Substrate for Measuring Lipase Activity and Present Polymer The step of mixing water or an aqueous solution with the mixture of the substrate for measuring lipase activity and the present polymer in the method for simplifying production of a substrate solution for measuring lipase activity according to the present invention is as described in the chapter <1>, the section "7. Step of Mixing Water or Aqueous Solution with Mixture of Substrate for Measuring Lipase Activity and Present Polymer".

8. Diameter of Micelles in Emulsion of Substrate Solution for Measuring Lipase Activity The diameter of micelles in an emulsion of a substrate solution for measuring lipase activity in the method for simplifying production of a substrate solution for measuring lipase activity according to the present invention is as described in the chapter <1>, the section "8. Diameter of Micelles in Emulsion of Substrate Solution for Measuring Lipase Activity".

<3> Reagent and Assay for Measuring Lipase Activity in Sample

The following describes a reagent for measuring lipase activity in a sample, which reagent includes a substrate solution for measuring lipase activity according to the present invention, and an assay for measuring lipase activity in a sample by using the substrate solution for measuring lipase activity according to the present invention.

1. Reagent for Measuring Lipase Activity in Sample (1) Components of Reagent for Measuring Lipase Activity in Sample The reagent for measuring lipase activity in a sample may consist of a substrate solution for measuring lipase activity according to the present invention. Alternatively, the reagent (reagent kit) may contain a substrate solution for measuring lipase activity according to the present invention as well as another reagent member.

Note that the reagent for measuring lipase activity in a sample is preferably a reagent kit containing a substrate solution for measuring lipase activity according to the present invention as well as another reagent member because of the following reasons (a) and (b).

(a) The substrate (DGGMR) for measuring lipase activity according to the present invention is stable at or near pH 4. By contrast, the lipase has optimal activity at or near pH 8. The respective suitable pH ranges are thus different.

(b) When an all-in-one reagent contains a substrate (DGGMR) for measuring lipase activity according to the present invention, a colipase, and, as a lipase promoter, bile acid or a salt thereof, the substrate (DGGMR) is unstable.

Thus, the reagent kit preferably comprises a substrate solution for measuring lipase activity according to the present invention and another reagent member. In this case, one reagent containing the substrate (DGGMR) for measuring lipase activity according to the present invention should have a pH at or near pH 4. At least one of the other reagent members combined with the above one reagent should have a pH of 8 or higher. In addition, it is preferable that the substrate (DGGMR) for measuring lipase activity according to the present invention, a colipase, and, as a lipase promoter, bile acid or a salt thereof are not included in one reagent.

Preferably, the reagent for measuring lipase activity in a sample is a two-component reagent kit consisting of a substrate solution for measuring lipase activity according to the present invention and another reagent member.

In this case, it is more preferable that another reagent member is used as the first reagent; and the substrate solution for measuring lipase activity according to the present invention is used as the second reagent.

In this case, it is still more preferable that another reagent member has a pH of 8 or higher; and the substrate solution for measuring lipase activity according to the present invention has a pH at or near pH 4.

In addition, both the colipase and the bile acid or salt thereof as a lipase promoter are not included in the substrate solution for measuring lipase activity according to the present invention. It is thus still more preferable that at least one of the colipase and the bile acid or salt thereof as a lipase promoter are included in another reagent member.

The reagent for measuring lipase activity in a sample, which reagent contains a substrate solution for measuring lipase activity according to the present invention, may be used to carry out measurement by an end-point method.

Alternatively, the reagent may be used to carry out measurement by a reaction rate method (rate method). The methods may be appropriately selected. Here, it is preferable to carry out measurement by the reaction rate method(rate method).

In addition, according to the present invention, the reagent for measuring lipase activity in a sample contains a substrate solution for measuring lipase activity. The substrate (DG-GMR) for measuring lipase activity according to the present invention is made to contact the sample so as to make a reaction. The lipase catalyzes hydrolysis to generate 1,2-o-dilauryl-rac-glycerol and glutaric acid (6'-methylresorufin) ester. This glutaric acid (6'-methylresorufin) ester is unstable and is thus hydrolyzed readily and naturally to give 6'-methylresorufin ($\lambda$max: 580 nm).

Accordingly, an increase in the resulting 6'-methylresorufin is measured by reading absorbance at or near 580 nm. Then, the activity value of the lipase contained in the sample can be determined. Note that this case may use a single-wavelength method or a two-wavelength method.

Meanwhile, the reagent for measuring lipase activity in a sample contains the substrate solution for measuring lipase activity according to the present invention. The temperature during the assay reaction may be set to a temperature e.g., 30° C. or 37° C. that is within a temperature range such that the reaction can proceed and reaction components e.g., an enzyme involving the assay reaction are not inactivated, denatured, or modified due to heat.

Meanwhile, the reagent for measuring lipase activity in a sample contains the substrate solution for measuring lipase activity according to the present invention. How to initiate the assay reaction may involve any of methods including: a method of adding, for example, a substrate for measuring lipase activity according to the present invention; a method of adding a sample; and the like.

Meanwhile, the reagent for measuring lipase activity in a sample contains the substrate solution for measuring lipase activity according to the present invention. The measurement may be performed manually or using a device (e.g., an automated analyzer).

In addition, regarding the reagent for measuring lipase activity in a sample, which reagent contains the substrate solution for measuring lipase activity according to the present invention, all or a part of the reagent members may be liquid.

Note that the substrate solution for measuring lipase activity according to the present invention, by itself, may be marketed and can be used for measuring lipase activity in a sample.

Note that the substrate solution for measuring lipase activity according to the present invention may be marketed in combination with another reagent member or other reagents and can be used for measuring lipase activity in a sample.

Examples of another reagent member and other reagents include: a buffer; a sample diluent; a reagent diluent; a reagent containing a substance used for calibration; and a reagent containing a substance used for quality control.

(2) Specific Examples of Reagent for Measuring Lipase Activity in Sample

The following illustrates specific examples of the reagent for measuring lipase activity in a sample, which reagent contains a substrate solution for measuring lipase activity according to the present invention.

(I) Example 1
(a) First Reagent (an aqueous solution (pH 8.3 at 20° C.) containing the following reagent components with the respective concentrations described below)
Sodium deoxycholate (a lipase promoter) 2% (w/v)
Calcium chloride (a lipase activator) 5 mM
Colipase (derived from a pig pancreas; Roche Diagnostics K. K. (Japan)) 375K Unit/L (5 mg/L)
Bicine (a buffer) 40 mM
(b) Second Reagent (a substrate solution for measuring lipase activity according to the present invention) (an aqueous solution (pH 4.0 at 20° C.) containing the following reagent components with the respective concentrations described below)
1,2-o-dilauryl-rac-glycero-3-glutaric acid (6'-methylresorufin) ester (DGGMR) (Roche Diagnostics K. K. (Japan)) (a substrate for measuring lipase activity) 0.3 mM
Side-chain-type nonreactive polyether-modified-type modified silicone oil 0.3% (w/v) L-Tartaric acid (a buffer) 40 mM (II) Example 2
(a) First Reagent (an aqueous solution (pH 8.4 at 20° C.) containing the following reagent components with the respective concentrations described below)
Sodium taurodeoxycholate (a lipase promoter) 2% (w/v)
Sodium deoxycholate (a lipase promoter) 0.2% (w/v)
Calcium chloride (a lipase activator) 5 mM
Colipase (derived from a pig pancreas; Roche Diagnostics K. K. (Japan)) 150K Unit/L (2 mg/L)
Tris(hydroxymethyl)aminomethane (Tris) (a buffer) 40 mM
(b) Second Reagent (a substrate solution for measuring lipase activity according to the present invention) (an aqueous solution containing the following reagent components with the respective concentrations described below)
1,2-o-dilauryl-rac-glycero-3-glutaric acid (6'-methylresorufin) ester (DGGMR) (Roche Diagnostics K. K. (Japan)) (a substrate for measuring lipase activity) 0.6 mM
Polyoxyethylene/polyoxypropylene condensate 2% (w/v)
Sodium taurodeoxycholate (a lipase promoter) 2% (w/v)

2. Assay for Measuring Lipase Activity in Sample
(1) How to Measure Lipase Activity in Sample The substrate solution for measuring lipase activity according to the present invention may be used for the assay in accordance with the assay for measuring lipase activity in a sample. In this case, the assay may be carried out by an end-point method. Alternatively, the assay may be carried out by a reaction rate method (rate method). The methods may be appropriately selected. Here, it is preferable to carry out the assay by the reaction rate method (rate method).

In addition, the substrate solution for measuring lipase activity according to the present invention may be used to carry out the measurement in accordance with the assay for measuring lipase activity in a sample. Regarding the measurement, a one-step method, in which measurement is carried out at one step, or a multi-step method, in which measurement is carried out at two or more steps, may be appropriately selected to carry out the measurement.

Note that the measuring reagent used for measuring lipase activity in a sample may be composed of the first reagent, the second reagent, and another reagent (one or more reagents). In this case, namely, the case having three or more reagents, the assay reaction can be performed using the number of steps required for the measurement using these reagents (as needed, two or more steps, or three or more steps), so that the lipase activity in the sample can be measured.

In addition, the substrate solution for measuring lipase activity according to the present invention may be used to carry out the measurement in accordance with the assay for measuring lipase activity in a sample. In this case, the substrate (DGGMR) for measuring lipase activity according to the present invention is made to contact the sample so as to make a reaction. The lipase catalyzes hydrolysis to generate 1,2-o-dilauryl-rac-glycerol and glutaric acid (6'-methylresorufin) ester. This glutaric acid (6'-methylresorufin) ester is unstable and is thus hydrolyzed readily and naturally to give 6'-methylresorufin (λmax: 580 nm).

Accordingly, an increase in the resulting 6'-methylresorufin is measured by reading absorbance at or near 580 nm. Then, the activity value of the lipase contained in the sample can be determined. Note that this case may use a single-wavelength method or a two-wavelength method.

Note that the activity value of the lipase contained in the sample is calculated from the absorbance (or transmittance) measured or a change in the absorbance (or transmittance). This calculation procedure may use absorbance (or transmittance) as measured on the basis of the molar absorption coefficient of 6'-methylresorufin. Alternatively, in this calculation procedure, the absorbance (or transmittance) of interest is compared with the absorbance (or transmittance) of a reference material (e.g., a standard solution or reference serum), the lipase activity value of which is known. These procedures may be suitably selected.

In addition, the activity value of the lipase contained in the sample is preferably calculated by subtracting the blank value from the absorbance (or transmittance) obtained by measuring the sample.

In addition, the substrate solution for measuring lipase activity according to the present invention may be used to carry out the measurement in accordance with the assay for measuring lipase activity in a sample. The temperature during the assay reaction may be set to a temperature e.g., 30° C. or 37° C. that is within a temperature range such that the assay reaction can proceed and reaction components e.g., an enzyme involving the assay reaction are not inactivated, denatured, or modified due to heat.

In addition, the substrate solution for measuring lipase activity according to the present invention may be used to carry out the assay in accordance with the assay for measuring lipase activity in a sample. In this case, how to initiate the assay reaction may involve any of methods including: a method of adding, for example, a substrate for measuring lipase activity according to the present invention; a method of adding a sample; and the like.

In addition, the substrate solution for measuring lipase activity according to the present invention may be used to carry out the measurement in accordance with the assay for measuring lipase activity in a sample. In this case, the measurement may be performed manually or using a device e.g., an automated analyzer.

(2) Specific Examples of Assay for Measuring Lipase Activity in Sample

The following illustrates specific examples of the assay for measuring lipase activity in a sample by using a substrate solution for measuring lipase activity according to the present invention.

(a) Measuring Reagent
(i) First Reagent

The first reagent described in the above section 1.(2)(I)(a) was used as the first reagent in this specific example regarding the measuring assay.

(ii) Second Reagent

The second reagent described in the above section 1.(2)(I)(b) was used as the second reagent in this specific example regarding the measuring assay.

(b) Sample

Human serum was used as a sample.

(c) Measurement
(i) First Step

The above sample and the first reagent are mixed to prepare a mixed liquid.

The amount of each of the sample and the first reagent mixed may be appropriately determined depending on the amount of the second reagent, the activity value of the lipase contained in the sample, and other conditions.

Note that, generally speaking, examples of the amount of the sample is preferably within a range from 0.5 to 100 μL and the amount of the first reagent is preferably within a range from 20 to 1,000 μL.

This mixed liquid is so prepared and then incubated.

The incubation period is not particularly limited, and, usually, is preferably within 20 minutes, more preferably within 10 minutes, and still more preferably within 5 minutes.

In addition, the incubation temperature may be higher than a temperature at which the above mixed liquid can be frozen.

Note that, generally speaking, the higher the assay reaction temperature, the higher the reaction rate. This is preferable.

However, if the temperature is too high, the components (e.g., an enzyme) involving the assay reaction are denatured or inactivated. Accordingly, the incubation temperature should be a temperature less than the temperature at which the components (e.g., an enzyme) involving the assay reaction can be denatured or inactivated.

This incubation temperature, usually, is preferably from 2 to 70° C., more preferably from 20 to 37° C., and still more preferably from 30 to 37° C.

Note that if the components (e.g., an enzyme) involving the assay reaction are each a heat-resistant component (e.g., a thermostable enzyme), the temperature may be much higher.

This mixed liquid of the sample and the first reagent is prepared and incubated. Next, a lipase contained in the sample is in contact with the reagent components contained in the first reagent. These components, for example, then promote and activate the lipase activity.

(ii) Second Step

The "mixed liquid of the sample and the first reagent" prepared in the first step is mixed with the second reagent. This makes the final reaction solution.

The amount of the second reagent mixed may be appropriately determined depending on the amount of the sample, the amount of the first reagent, the activity value of the lipase contained in the sample, settings of an analyzer used, and other conditions.

Note that, generally speaking, the amount of the second reagent is, for example, preferably within a range from 10 to 1,000 μL.

This final reaction solution is so prepared and then incubated.

The incubation period is not particularly limited, and, usually, is preferably within 20 minutes, more preferably within 10 minutes, and still more preferably within 5 minutes.

In addition, the incubation temperature may be higher than a temperature at which the above final reaction solution can be frozen.

Note that, generally speaking, the higher the assay reaction temperature, the higher the reaction rate. This is preferable.

However, if the temperature is too high, the components (e.g., an enzyme) involving the assay reaction are denatured or inactivated. Accordingly, the incubation temperature should be a temperature less than the temperature at which the components (e.g., an enzyme) involving the assay reaction are denatured or inactivated.

This incubation temperature, usually, is preferably from 2 to 70° C., more preferably from 20 to 37° C., and still more preferably from 30 to 37° C.

Note that if the components (e.g., an enzyme) involving the assay reaction are each a heat-resistant component (e.g., a thermostable enzyme), the temperature may be much higher.

Through the preparation and incubation of the final reaction solution, the lipase activity is promoted and activated at the first step and, at the second step, the assay reaction is initiated, so that the reaction proceeds so as to measure the lipase activity in the sample.

Specifically, the present invention provides the process for producing a substrate solution for measuring lipase activity. Here, the second reagent (the substrate solution for measuring lipase activity according to the present invention) is an emulsified substrate solution composed of stable and uniform micelle particles, and, in the second step, is made to contact a lipase contained in a sample. This lipase catalyzes hydrolysis to generate, from the substrate (DGGMR) for measuring lipase activity, 1,2-o-dilauryl-rac-glycerol and glutaric acid (6'-methylresorufin) ester.

This glutaric acid (6'-methylresorufin) ester is unstable and is thus hydrolyzed readily and naturally to give 6'-methylresorufin (λmax: 580 nm).

The resulting 6'-methylresorufin has a maximum absorption wavelength (λmax) at 580 nm. The absorbance (or transmittance) (due to this 6'-methylresorufin) of the final reaction solution is measured by reading absorbance (or transmittance) at or near 580 nm.

Next, the activity value of the lipase contained in the sample is calculated from the absorbance (or transmittance) measured or a change in the absorbance (or transmittance).

Note that this calculation procedure may use absorbance (or transmittance) as measured on the basis of the molar absorption coefficient of 6'-methylresorufin. Alternatively, in this calculation procedure, the absorbance (or transmittance) of interest is compared with the absorbance (or transmittance) of a reference material (e.g., a standard solution or reference serum), the lipase activity value of which is known. These procedures may be suitably selected.

Note that the activity value of the lipase contained in the sample is preferably calculated using the absorbance difference (ΔAbs.) determined by subtracting the blank value from the absorbance (or transmittance) of the final reaction solution as obtained by measuring the sample.

EXAMPLES

The following specifically describes the present invention in detail by referring to Examples. The present invention, however, is not limited to these Examples.

Example 1(Production (1) of Substrate Solution for Measuring Lipase Activity)

The clouding point of the present polymer was measured. A substrate solution for measuring lipase activity was produced in accordance with the process of the present invention. Also, the diameter of micelles in an emulsion of the substrate solution for measuring lipase activity was determined.

1. Measurement of Clouding Point (1) Preparation of Aqueous Solution Containing Present Polymer The following four kinds (a) to (d) of a side-chain-type nonreactive modified silicone oil (polyether modified type) and the following two kinds (e) to (f) of a polyoxyethylene/polyoxypropylene condensate were each mixed with pure water such that the concentration was 0.1% (w/v). Accordingly, an aqueous solution containing the present polymer was prepared.

(a) KF-351A (the distributor: Shin-Etsu Chemical Co., Ltd. (Japan))

(b) KF-354L (the distributor: Shin-Etsu Chemical Co., Ltd. (Japan))

(c) KF-355A (the distributor: Shin-Etsu Chemical Co., Ltd. (Japan))

(d) KF-6011 (the distributor: Shin-Etsu Chemical Co., Ltd. (Japan))

(e) Pluronic L-34 (the distributor: ADEKA CORPORATION (Japan))

(f) Pluronic L-44 (the distributor: ADEKA CORPORATION (Japan))

(2) Measurement of Clouding Point of Present Polymer (i) The 6 kinds (a) to (f) of the aqueous solution containing the present polymer (the concentration: 0.1% (w/v)) as prepared in the above (1) were each poured in an individual 1-mL test tube.

(ii) Next, these test tubes were placed in a thermostat water tank (the model: BK-33; the distributor: YAMATO SCIENTIFIC CO., LTD. (Japan)), and the temperature of the water tank was increased by 1° C. at a time. Note that the temperature of the water tank was measured with a mercury thermometer.

(iii) Then, the present polymer-containing aqueous solution in each test tube placed in the thermostat water tank was observed. The temperature at which this aqueous solution became clouded was recorded as the clouding point of the present polymer.

Note that in the thermostat water tank (BK-33) used for the measurement of the clouding point, the upper limit of the temperature at which the water tank can be heated is 77° C. So, when the aqueous solution did not become clouded and the clouding point was not reached even after the temperature of the water tank was raised to 77° C., the record was designated as "Over 77° C.".

(3) Measured Results

The clouding point of each present polymer as measured and recorded in the above (2) was listed below.

(a) KF-351A: 52° C.
(b) KF-354L: Over 77° C.
(c) KF-355A: 67° C.
(d) KF-6011: 64° C.
(e) Pluronic L-34: 65° C.
(f) Pluronic L-44: 67° C.

2. Production of Substrate Solution for Measuring Lipase Activity According to Present Invention A substrate solution for measuring lipase activity was produced in accordance with the process for producing a substrate solution for measuring lipase activity and the method for simplifying production of a substrate solution for measuring lipase activity according to the present invention.

(1) First, 0.09 g of 1,2-o-dilauryl-rac-glycero-3-glutaric acid (6'-methylresorufin) ester (DGGMR) (the distributor:

Roche Diagnostics K. K. (Japan)), a substrate for measuring lipase activity according to the present invention, was weighed and placed in each of 6 beakers (the volume: 10 mL).

(2) Next, 4.0 g of each of the following 4 kinds (a) to (d) of the side-chain-type nonreactive modified silicone oil (polyether modified type) and the following 2 kinds (e) to (f) of the polyoxyethylene/polyoxypropylene condensate was weighed and added to one of the different beakers used in the above (1).

(a) KF-351A (the distributor: Shin-Etsu Chemical Co., Ltd. (Japan))

(b) KF-354L (the distributor: Shin-Etsu Chemical Co., Ltd. (Japan))

(c) KF-355A (the distributor: Shin-Etsu Chemical Co., Ltd. (Japan))

(d) KF-6011 (the distributor: Shin-Etsu Chemical Co., Ltd. (Japan))

(e) Pluronic L-34 (the distributor: ADEKA CORPORATION (Japan))

(f) Pluronic L-44 (the distributor: ADEKA CORPORATION (Japan))

(3) After the addition in the above (2), each beaker was placed in a thermostat water tank (the model: BK-33; the distributor: YAMATO SCIENTIFIC CO., LTD. (Japan)) set at a temperature of 67° C. Then, each beaker was stirred and the substrate (DGGMR) for measuring lipase activity and the present polymer were mixed at 67° C. Note that the temperature of the water tank was measured and checked with a mercury thermometer.

This mixing (stirring) at 67° C. was performed for 5 minutes to prepare a "mixture of the substrate (DGGMR) for measuring lipase activity and the present polymer".

Note that each beaker was placed on a stirrer (a remote-driven electromagnetic stirrer; the model: HP40107; the distributor: Sansho Co., Ltd. (Japan)) in the water tank at a temperature of 67° C. while this stirring was performed. A magnet bar in each beaker was rotated while the dial of a control unit of this stirrer was set to "3".

(4) Next, all of the "mixture of the substrate (DGGMR) for measuring lipase activity and the present polymer" as described in the above (3) was aspirated using a micropipette from each beaker. All (all the amount) of the mixture was added from the micropipette to a "certain quantity (4.0 mL) of pure water", which had been kept at 20° C. in another beaker (the volume: 10 mL), under stirring.

After the addition, this stirring was continued at room temperature (25° C.) for 5 minutes. In this way, the "certain quantity (4.0 mL) of pure water" was mixed with (all) the "mixture prepared by mixing the substrate (DGGMR) for measuring lipase activity and the present polymer".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

Meanwhile, the temperature of the "certain quantity (4.0 mL) of pure water" in each beaker was measured with a mercury thermometer, and whether or not the temperature was 20° C. was checked.

(5) Next, the "mixed liquid after the mixture (the mixture of the substrate (DGGMR) for measuring lipase activity and the present polymer) and the certain quantity of pure water had been mixed" as described in the above (4) was further mixed with a certain quantity of pure water to have a final volume of 200 mL.

(6) The above procedure allowed for production of all the following six kinds (a) to (f) of the substrate solution for measuring lipase activity in accordance with the production process and the production-simplifying method according to the present invention.

Note that in any of (all the 6 kinds of) these substrate solutions for measuring lipase activity, the substrate (DGGMR) for measuring lipase activity had a concentration of 0.6 mM and the present polymer had a concentration of 2.0% (w/v).

In addition, there was neither an observable concentration gradient nor strong turbidity in any of (all the six kinds of) these substrate solutions for measuring lipase activity. In this way, whether or not each substrate solution was mixed uniformly was visually inspected.

(a) Substrate solution (a) for measuring lipase activity (the substrate for measuring lipase activity: DGGMR; the present polymer: KF-351A)

(b) Substrate solution (b) for measuring lipase activity (the substrate for measuring lipase activity: DGGMR; the present polymer: KF-354L)

(c) Substrate solution (c) for measuring lipase activity (the substrate for measuring lipase activity: DGGMR; the present polymer: KF-355A)

(d) Substrate solution (d) for measuring lipase activity (the substrate for measuring lipase activity: DGGMR; the present polymer: KF-6011)

(e) Substrate solution (e) for measuring lipase activity (the substrate for measuring lipase activity: DGGMR; the present polymer: Pluronic L-34)

(f) Substrate solution (f) for measuring lipase activity (the substrate for measuring lipase activity: DGGMR; the present polymer: Pluronic L-44)

3. Measuring Diameter of Micelles in Emulsion of Substrate Solution for Measuring Lipase Activity The diameter of micelles in an emulsion of (all the 6 kinds of) the substrate solution for measuring lipase activity as produced in the above section 2 was determined.

(1) Measuring Diameter of Micelles in Emulsion (i) Each individual plastic cell contained 2.5 mL of each of the 6 kinds ((a) to (f) of the above section 2.(7)) of the substrate solution for measuring lipase activity (the substrate (DGGMR) for measuring lipase activity had a concentration of 0.6 mM; the present polymer had a concentration of 2.0% (w/v)) as produced in the above section 2.

(ii) Next, each plastic cell was placed in a dynamic light-scattering particle size distribution analyzer (the model: LB-550; the distributor: Horiba, Ltd. (Japan)). Then, the diameter (particle size) of micelles in an emulsion of each substrate solution for measuring lipase activity was measured in each plastic cell. Note that the measurement was conducted at room temperature (25° C.).

(2) Measured Results

Table 1 shows the diameter (particle size) of micelles in an emulsion of each of the 6 kinds of the substrate solution for measuring lipase activity as measured in the above (1).

Note that Table 1 indicates the averaged diameter (particle size) of micelles in an emulsion of each of the 6 kinds of the substrate solution for measuring lipase activity.

In addition, Table 1 also shows the observation results of how the 6 kinds of the substrate solution for measuring lipase activity looked visually. Further, Table 1 shows the results of measuring the clouding point of the present polymer used in each of the 6 kinds of the substrate solution for measuring lipase activity as determined in the section 1.

Note that in the column "Observation Results" in this table, "○" indicates that "neither a concentration gradient, strong turbidity, nor coloring was observed".

Meanwhile, in the column "Clouding Point of Present Polymer Used" in this table, the measured value of the clouding point of the present polymer used in each substrate solution for measuring lipase activity was designated. When the substrate solution did not become clouded and the clouding point was not reached even after the temperature of the water tank was raised to 77° C., the space was filled in with "Over 77° C.".

TABLE 1

| | Present Invention | | | |
|---|---|---|---|---|
| Substrate Solution for Measuring Lipase Activity | Present Polymer | (Averaged) Diameter (Particle Size) of Micelles in Emulsion | Observation Results | Clouding Point of Present Polymer Used |
| Substrate Solution (a) for Measuring Lipase Activity | KF-351A | 514.6 nm | ○ | 52° C. |
| Substrate Solution (b) for Measuring Lipase Activity | KF-354L | 564.5 nm | ○ | Over 77° C. |
| Substrate Solution (c) for Measuring Lipase Activity | KF-355A | 115.9 nm | ○ | 67° C. |
| Substrate Solution (d) for Measuring Lipase Activity | KF-6011 | 151.4 nm | ○ | 64° C. |
| Substrate Solution (e) for Measuring Lipase Activity | Pluronic L-34 | 1,063.9 nm | ○ | 65° C. |
| Substrate Solution (f) for Measuring Lipase Activity | Pluronic L-44 | 109.1 nm | ○ | 67° C. |

Observation results
○: neither a concentration gradient, strong turbidity, nor coloring was observed.

(3) Discussion

Table 1 demonstrates that regarding the 6 kinds of the substrate solutions for measuring lipase activity (i.e., the substrate solutions (a) to (f) for measuring lipase activity) as produced in accordance with the production process and the production-simplifying method according to the present invention, the diameter (particle size) of micelles in each emulsion ranges from 100 nm to 1,100 nm.

That is, the diameter (particle size) of micelles was measured as described above. The results demonstrate that any of the six kinds of the substrate solution for measuring lipase activity is composed of micelle particles and is produced as an emulsified substrate solution for measuring lipase activity.

In any of the 6 kinds of the substrate solution for measuring lipase activity, the diameter (particle size) of micelles in each emulsion is found to be within a range from 60 nm to 1,500 nm, in which range the rate of reaction with a lipase is high, the resulting emulsion is stable, and the substrate solution for measuring lipase activity can be stored and used for a long period.

In addition, Table 1 shows that there was neither an observable concentration gradient, strong turbidity, nor coloring in any of the 6 kinds of the substrate solution for measuring lipase activity. Hence, no such problems were found.

The above demonstrates that the process for producing a substrate solution for measuring lipase activity according to the present invention, the method for simplifying production of a substrate solution for measuring lipase activity according to the present invention, and the substrate solutions for measuring lipase activity as produced in accordance with the process and the method are characterized by the following points (i) to (iii).

(i) In conventional processes, a substrate for measuring lipase activity is mixed into a solution containing an organic solvent (e.g., an alcohol); a liquid containing a substrate for measuring lipase activity is added dropwise and mixed into a solution; a liquid containing a substrate for measuring lipase activity is jet-injected into a solution; a substrate solution for measuring lipase activity is stirred using a strong mixer at a high speed; a substrate solution for measuring lipase activity is subjected to ultrasonication; or the like. In the present invention, the mixing does not necessitate cumbersome or special processing such that skill is required, or does not necessitate a special apparatus or other items.

(ii) The substrate solution for measuring lipase activity can be stirred, for example, using a common mixer at a typical speed, and can thus be produced using a simple, short, and inexpensive procedure. Hence, the production of the substrate solution for measuring lipase activity can be simplified.

(iii) The substrate solution for measuring lipase activity produced is suitable for the measurement of lipase activity in a sample.

Example 2(Production (2) of Substrate Solution for Measuring Lipase Activity)

A substrate solution for measuring lipase activity was produced in accordance with the process of the present invention and a control process. Also, the diameter of micelles in an emulsion of the substrate solution for measuring lipase activity was determined.

1. Production of Substrate Solution for Measuring Lipase Activity

A substrate solution for measuring lipase activity was produced in accordance with the process for producing a substrate solution for measuring lipase activity and the method for simplifying production of a substrate solution for measuring lipase activity according to the present invention.

In addition, a substrate solution for measuring lipase activity was produced in accordance with the control process.

<1> Production of Substrate Solution for Measuring Lipase Activity in Accordance with Process of the Present Invention.

(1) First, 0.09 g of 1,2-o-dilauryl-rac-glycero-3-glutaric acid (6'-methylresorufin) ester (DGGMR) (the distributor: Roche Diagnostics K. K. (Japan)), a substrate for measuring lipase activity according to the present invention, was weighed and placed in each of 5 beakers (the volume: 10 mL).

(2) Next, 4.0 g of each of the following 3 kinds (a) to (c) of the side-chain-type nonreactive modified silicone oil (polyether modified type) and the following 2 kinds (d) to (e) of the polyoxyethylene/polyoxypropylene condensate was weighed and added to one of the different beakers used in the above (1).

(a) KF-351A (the distributor: Shin-Etsu Chemical Co., Ltd. (Japan))

(b) KF-355A (the distributor: Shin-Etsu Chemical Co., Ltd. (Japan))

(c) KF-6011 (the distributor: Shin-Etsu Chemical Co., Ltd. (Japan))

(d) Pluronic L-34 (the distributor: ADEKA CORPORATION (Japan))

(e) Pluronic L-44 (the distributor: ADEKA CORPORATION (Japan))

(3) After the addition as described in the above (2), each beaker was subjected to stirring at room temperature (25° C.). Then, each beaker was stirred and the substrate (DGGMR) for measuring lipase activity and the present polymer were mixed in each beaker.

This mixing (stirring) was performed for 5 minutes to prepare a "mixture of the substrate (DGGMR) for measuring lipase activity and the present polymer".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

(4) Next, a micropipette was used to add a "certain quantity (4.0 mL) of 2% (w/v) concentration of sodium taurodeoxycholate aqueous solution" at room temperature (25° C.) under stirring to (all) the "mixture of the substrate (DGGMR) for measuring lipase activity and the present polymer" in the beaker as described in the above (3).

After the addition, this stirring was continued at room temperature (25° C.) for 5 minutes. In this way, the "certain quantity (4.0 mL) of 2% (w/v) sodium taurodeoxycholate aqueous solution" was mixed with (all) the "mixture prepared by mixing the substrate (DGGMR) for measuring lipase activity and the present polymer".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

(5) Next, an additional certain quantity of 2% (w/v) sodium taurodeoxycholate aqueous solution was further mixed with the "mixed liquid after the mixture (the mixture of the substrate (DGGMR) for measuring lipase activity and the present polymer) and the certain quantity of 2% (w/v) sodium taurodeoxycholate aqueous solution had been mixed" as described in the above (4) to have a final volume of 200 mL.

(6) The above procedure allowed for production of all the following five kinds (A) to (E) of the substrate solution for measuring lipase activity in accordance with the production process and the production-simplifying method according to the present invention.

Note that in any of (all the 5 kinds of) these substrate solutions for measuring lipase activity, the substrate (DGGMR) for measuring lipase activity had a concentration of 0.6 mM and the present polymer had a concentration of 2.0% (w/v).

In addition, there was neither an observable concentration gradient nor strong turbidity in any of (all the five kinds of) these substrate solutions for measuring lipase activity. In this way, whether or not each substrate solution was mixed uniformly was visually inspected.

(A) Substrate solution (A) for measuring lipase activity (the substrate for measuring lipase activity: DGGMR; the present polymer: KF-351A)

(B) Substrate solution (B) for measuring lipase activity (the substrate for measuring lipase activity: DGGMR; the present polymer: KF-355A)

(C) Substrate solution (C) for measuring lipase activity (the substrate for measuring lipase activity: DGGMR; the present polymer: KF-6011)

(D) Substrate solution (D) for measuring lipase activity (the substrate for measuring lipase activity: DGGMR; the present polymer: Pluronic L-34)

(E) Substrate solution (E) for measuring lipase activity (the substrate for measuring lipase activity: DGGMR; the present polymer: Pluronic L-44)

<2> Production of Substrate Solution for Measuring Lipase Activity in Accordance with Control Process.

(1) First, 0.09 g of 1,2-o-dilauryl-rac-glycero-3-glutaric acid (6'-methylresorufin) ester (DGGMR) (the distributor: Roche Diagnostics K. K. (Japan)), a substrate for measuring lipase activity, was weighed and placed in each of 5 beakers (the volume: 10 mL).

(2) Next, 4.0 g of each of the following kinds (f) to (j) of a surfactant (each was a nonionic surfactant) was weighed and added to one of the different beakers used in the above (1).

(f) Tween 80 (polyoxyethylene sorbitan monooleate) (the distributor: TOKYO CHEMICAL INDUSTRY CO., LTD. (Japan))

(g) NIKKOL GO-460V (polyoxyethylene (60) tetraoleate sorbitol) (the distributor: Nikko Chemicals Co., Ltd. (Japan))

(h) NIKKOL TL-10 (mono-coconut oil fatty acid polyoxyethylene (20) sorbitol) (the distributor: Nikko Chemicals Co., Ltd. (Japan))

(i) SANNIX GP-1000 (polyoxypropylene glyceryl ether) (the distributor: Sanyo Chemical Industries, Ltd. (Japan))

(j) NIKKOL TMGO-15 (polyoxyethylene (15) monooleate glyceryl) (the distributor: Nikko Chemicals Co., Ltd. (Japan))

(3) After the addition as described in the above (2), each beaker was stirred at room temperature (25° C.), and the substrate (DGGMR) for measuring lipase activity and each surfactant were mixed in each beaker.

This mixing (stirring) was performed for 5 minutes to prepare a "mixture of the substrate (DGGMR) for measuring lipase activity and each surfactant".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

(4) Next, a micropipette was used to add a "certain quantity (4.0 mL) of 2% (w/v) concentration of sodium taurodeoxycholate aqueous solution" at room temperature (25° C.) under stirring to (all) the "mixture of the substrate (DGGMR) for measuring lipase activity and each surfactant" in the beaker as described in the above (3).

After the addition, this stirring was continued at room temperature (25° C.) for 5 minutes. In this way, the "certain quantity (4.0 mL) of 2% (w/v) sodium taurodeoxycholate aqueous solution" was mixed with (all) the "mixture prepared by mixing the substrate (DGGMR) for measuring lipase activity and each surfactant".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

(5) Next, an additional certain quantity of 2% (w/v) sodium taurodeoxycholate aqueous solution was further mixed with the "mixed liquid after the mixture (the mixture of the substrate (DGGMR) for measuring lipase activity and each surfactant) and the certain quantity of 2% (w/v) sodium taurodeoxycholate aqueous solution had been mixed" as described in the above (4) to have a final volume of 200 mL.

(6) The above procedure allowed for production of all the following five kinds (F) to (J) of the substrate solution for measuring lipase activity in accordance with the control process.

Note that in any of (all the 5 kinds of) these substrate solutions for measuring lipase activity, the substrate (DGGMR) for measuring lipase activity had a concentration of 0.6 mM and each surfactant had a concentration of 2.0% (w/v).

(F) Substrate solution (F) for measuring lipase activity (the substrate for measuring lipase activity: DGGMR; the surfactant: Tween 80)

(G) Substrate solution (G) for measuring lipase activity (the substrate for measuring lipase activity: DGGMR; the surfactant: NIKKOL GO-460V)

(H) Substrate solution (H) for measuring lipase activity (the substrate for measuring lipase activity: DGGMR; the surfactant: NIKKOL TL-10)

(I) Substrate solution (I) for measuring lipase activity (the substrate for measuring lipase activity: DGGMR; the surfactant: SANNIX GP-1000)

(J) Substrate solution (J) for measuring lipase activity (the substrate for measuring lipase activity: DGGMR; the surfactant: NIKKOL TMGO-15)

Note that any of the above "(F) Substrate solution (F) for measuring lipase activity", "(G) Substrate solution (G) for measuring lipase activity", and "(H) Substrate solution (H) for measuring lipase activity" had neither an observable concentration gradient nor strong turbidity, and was uniformly mixed, which was checked visually.

However, the above "(I) Substrate solution (I) for measuring lipase activity" was strongly turbid. In addition, in the above "(J) Substrate solution (J) for measuring lipase activity", coloring occurred.

2. Measuring Diameter of Micelles in Emulsion of Substrate Solution for Measuring Lipase Activity With respect to the 5 kinds ((A) to (E) of the above section 1.<1>(7)) of the substrate solution for measuring lipase activity produced by the process of the present invention and the 4 kinds ((F) to (I) of the above section 1.<2>(7)) of the substrate solution for measuring lipase activity produced by the control process, the diameter of micelles in each emulsion was measured (note that because coloring occurred in the "(J) Substrate solution (J) for measuring lipase activity", the diameter of micelles in an emulsion thereof was not determined).

(1) Measuring Diameter of Micelles in Emulsion (i) Each individual plastic cell contained 2 mL of each of the 5 kinds ((A) to (E) of the above section 1.<1>(7)) of the substrate solution for measuring lipase activity (for each, the substrate (DGGMR) for measuring lipase activity had a concentration of 0.6 mM; the present polymer had a concentration of 2.0% (w/v)) produced in the above section 1.<1> and the 4 kinds ((F) to (I) of the above section 1.<2>(7)) of the substrate solution for measuring lipase activity (for each, the substrate (DGGMR) for measuring lipase activity had a concentration of 0.6 mM; the surfactant had a concentration of 2.0% (w/v)) produced in the above section 1.<2>.

(ii) Next, an optical probe (optical fiber) of a dynamic light-scattering particle size distribution analyzer (the model: Nanotrac UPA-EX250; the distributor: NIKKISO CO., LTD. (Japan)) was inserted into each plastic cell one by one. Then, the diameter (particle size) of micelles in an emulsion of each substrate solution for measuring lipase activity was measured in each plastic cell. Note that the measurement was conducted at room temperature (25° C.).

(2) Measured Results

Table 2 shows the diameter (particle size) of micelles in an emulsion of each of the 9 kinds of the substrate solution for measuring lipase activity as measured in the above (1).

Note that Table 2 indicates the averaged diameter (particle size) of micelles in an emulsion of each of the 9 kinds of the substrate solution for measuring lipase activity.

In addition, Table 2 shows the visual observation results of (the total of 5 kinds of) the substrate solution for measuring lipase activity produced in the above section 1.<1> by the process of the present invention and (the total of 5 kinds of) the substrate solution for measuring lipase activity produced in the section 1.<2> by the control process.

Note that in the column "Observation Results" in this table, "○" indicates that "neither a concentration gradient, strong turbidity, nor coloring was observed". The "×(*1)" indicates that "strong turbidity occurred" and the "×(*2)" indicates that "coloring occurred".

TABLE 2

| Substrate Solution for Measuring Lipase Activity | | (Averaged) Diameter (Particle Size) of Micelles in Emulsion | Observation Results |
|---|---|---|---|
| Present Invention | | | |
| | Present Polymer | | |
| Substrate Solution (A) for Measuring Lipase Activity | KF-351A | 147 nm | ○ |
| Substrate Solution (B) for Measuring Lipase Activity | KF-355A | 156 nm | ○ |
| Substrate Solution (C) for Measuring Lipase Activity | KF-6011 | 105 nm | ○ |
| Substrate Solution (D) for Measuring Lipase Activity | Pluronic L-34 | 112 nm | ○ |
| Substrate Solution (E) for Measuring Lipase Activity | Pluronic L-44 | 89 nm | ○ |
| Control | | | |
| | Surfactant | | |
| Substrate Solution (F) for Measuring Lipase Activity | Tween80 | 41 nm | ○ |
| Substrate Solution (G) for Measuring Lipase Activity | NIKKOL GO-460V | 51 nm | ○ |
| Substrate Solution (H) for Measuring Lipase Activity | NIKKOL TL-10 | 35 nm | ○ |
| Substrate Solution (I) for Measuring Lipase Activity | SANNIX GP-1000 | 213 nm | x (*1) |
| Substrate Solution (J) for Measuring Lipase Activity | NIKKOL TMGO-15 | (Not measured) | x (*2) |

Observation results
○: neither a concentration gradient, strong turbidity, nor coloring was observed.
x (*1): strong turbidity occurred.
x (*2): coloring occurred.

(3) Discussion (I) Substrate Solution for Measuring Lipase Activity Produced by Process of the Present Invention Table 2 demonstrates that regarding the 5 kinds of the substrate solutions for measuring lipase activity (i.e., the substrate solutions (A) to (E) for measuring lipase activity) produced in accordance with the production process and the production-simplifying method according to the present invention, the diameter (particle size) of micelles in each emulsion ranges from 80 nm to 200 nm.

That is, the diameter (particle size) of micelles was measured as described above. The results demonstrate that any of the 5 kinds of the substrate solution for measuring lipase activity is composed of micelle particles and is produced as an emulsified substrate solution for measuring lipase activity.

In any of the 5 kinds of the substrate solution for measuring lipase activity, the diameter (particle size) of micelles in each emulsion is found to be within a range from 60 nm to 1,500 nm, in which range the rate of reaction with a lipase is high, the resulting emulsion is stable, and the substrate solution for measuring lipase activity can be stored and used for a long period.

In addition, Table 2 shows that there was neither an observable concentration gradient, strong turbidity, nor coloring in any of the 5 kinds of the substrate solution for measuring lipase activity produced in accordance with the production process and the production-simplifying method according to the present invention. Hence, no such problems were found.

The above demonstrates that the process for producing a substrate solution for measuring lipase activity according to the present invention, the method for simplifying production of a substrate solution for measuring lipase activity according to the present invention, and the substrate solutions as produced in accordance with the process and the method are characterized by the following points (i) to (iii).

(i) In conventional processes, a substrate for measuring lipase activity is mixed into a solution containing an organic solvent (e.g., an alcohol); a liquid containing a substrate for measuring lipase activity is added dropwise and mixed into a solution; a liquid containing a substrate for measuring lipase activity is jet-injected into a solution; a substrate solution for measuring lipase activity is stirred using a strong mixer at a high speed; a substrate solution for measuring lipase activity is subjected to ultrasonication; or the like. In the present invention, the mixing does not necessitate cumbersome or special processing such that skill is required, or does not necessitate a special apparatus or other items.

(ii) The substrate solution for measuring lipase activity can be stirred, for example, using a common mixer at a typical speed, and can thus be produced using a simple, short, and inexpensive procedure. Hence, the production of the substrate solution for measuring lipase activity can be simplified.

(iii) The substrate solution for measuring lipase activity produced is suitable for the measurement of lipase activity in a sample.

(II) Substrate Solution for Measuring Lipase Activity Produced by Control Process Table 2 demonstrates that regarding the "(F) substrate solution (F) for measuring lipase activity", the "(G) substrate solution (G) for measuring lipase activity", and the "(H) substrate solution (H) for measuring lipase activity" produced in accordance with the control process, the diameter (particle size) of micelles in each emulsion is less than 60 nm.

That is, in any of (the total of three kinds of) these substrate solutions for measuring lipase activity produced by the control process, the diameter (particle size) of micelles thereof was measured. The results demonstrate that any of them is produced as an emulsified substrate solution for measuring lipase activity that is composed of micelle particles.

However, any of (all the 3 kinds of) these substrate solutions for measuring lipase activity produced by the control process, the diameter (particle size) of micelles in each emulsion is out of the range from 60 nm to 1,500 nm, in which range the rate of reaction with a lipase is high, the resulting emulsion is stable, and the substrate solution for measuring lipase activity can be stored and used for a long period.

That is, any of (the total of three kinds of) these substrate solutions for measuring lipase activity produced by the control process is found to be unsuitable for measuring lipase activity in a sample.

(b) In addition, as described in Table 2, strong turbidity occurred in the "(I) Substrate solution (I) for measuring lipase activity" produced by the control process. In addition, in the "(J) Substrate solution (J) for measuring lipase activity", coloring occurred.

That is, any of (the total of two kinds of) these substrate solutions for measuring lipase activity produced by the control process is found to be unsuitable for measuring lipase activity in a sample.

Example 3 (Production (3) of Substrate Solution for Measuring Lipase Activity)

Also, substrate solutions for measuring lipase activity were produced in accordance with the process of the present invention and the control process and the diameter of micelles in an emulsion of each substrate solution for measuring lipase activity was determined.

1. Producing Substrate Solution for Measuring Lipase Activity

Substrate solutions for measuring lipase activity were produced in accordance with the process for producing a substrate solution for measuring lipase activity and the method for simplifying production of a substrate solution for measuring lipase activity according to the present invention.

In addition, substrate solutions for measuring lipase activity were produced in accordance with the control process.

<1> Production of Substrate Solution for Measuring Lipase Activity in Accordance with Process of the Present Invention.

(1) First, 0.09 g of 1,2-o-dilauryl-rac-glycero-3-glutaric acid (6'-methylresorufin) ester (DGGMR) (the distributor: Roche Diagnostics K. K. (Japan)), a substrate for measuring lipase activity according to the present invention, was weighed and placed in each of 4 beakers (the volume: 10 mL).

(2) Next, 2.0 g of each of the following 2 kinds (a) to (b) of the side-chain-type nonreactive modified silicone oil (polyether modified type) was weighed and added to one of the different beakers used in the above (1). In addition, 4.0 g of each of the following 2 kinds (a) to (b) of the side-chain-type nonreactive modified silicone oil (polyether modified type) was weighed and added to one of the different beakers used in the above (1) (specifically, for each of the present polymers, one beaker, in which 2.0 g of the present polymer was weighed and added, and another beaker, in which 4.0 g of the present polymer was weighed and added, were prepared).

(a) KF-351A (the distributor: Shin-Etsu Chemical Co., Ltd. (Japan))

(b) KF-6011 (the distributor: Shin-Etsu Chemical Co., Ltd. (Japan))

(3) After the addition as described in the above (2), each beaker was stirred at room temperature (25° C.), and the substrate (DGGMR) for measuring lipase activity and the present polymer were mixed in each beaker.

This mixing (stirring) was performed for 5 minutes to prepare a "mixture of the substrate (DGGMR) for measuring lipase activity and the present polymer".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

(4) Next, a micropipette was used to add a "certain quantity (4.0 mL) of pure water" at room temperature (25° C.) under stirring to (all) the "mixture of the substrate (DGGMR) for measuring lipase activity and the present polymer" in the beaker as described in the above (3).

After the addition, this stirring was continued at room temperature (25° C.) for 5 minutes. In this way, the "certain quantity (4.0 mL) of pure water" was mixed with (all) the mixture prepared by mixing the substrate (DGGMR) for measuring lipase activity and the present polymer".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

(5) Next, the "mixed liquid after the mixture (the mixture of the substrate (DGGMR) for measuring lipase activity and the present polymer) and the certain quantity of pure water had been mixed" as described in the above (4) was further mixed with a certain quantity of pure water to have a final volume of 200 mL.

(6) The above procedure allowed for production of all the following 4 kinds [1] to [4] of the substrate solution for measuring lipase activity in accordance with the production process and the production-simplifying method according to the present invention.

Note that in any of (all the 4 kinds of) these substrate solutions for measuring lipase activity, the substrate (DGGMR) for measuring lipase activity had a concentration of 0.6 mM.

Meanwhile, the concentration of the present polymer was 1.0% (w/v) in the substrate solution for measuring lipase activity obtained by weighing 2.0 g of the present polymer and adding it to the beaker as described in the above (2). Then, the concentration of the present polymer was 2.0% (w/v) in the substrate solution for measuring lipase activity obtained by weighing 4.0 g of the present polymer and adding it to the beaker.

[1] Substrate solution [1] for measuring lipase activity (the substrate for measuring lipase activity: DGGMR; the present polymer: KF-351A (the concentration: 1.0% (w/v))

[2] Substrate solution [2] for measuring lipase activity (the substrate for measuring lipase activity: DGGMR; the present polymer: KF-351A (the concentration: 2.0% (w/v))

[3] Substrate solution [3] for measuring lipase activity (the substrate for measuring lipase activity: DGGMR; the present polymer: KF-6011 (the concentration: 1.0% (w/v))

[4] Substrate solution [4] for measuring lipase activity (the substrate for measuring lipase activity: DGGMR; the present polymer: KF-6011 (the concentration: 2.0% (w/v))

<2> Production of Substrate Solution for Measuring Lipase Activity in Accordance with Control Process.

(1) First, 0.09 g of 1,2-o-dilauryl-rac-glycero-3-glutaric acid (6'-methylresorufin) ester (DGGMR) (the distributor: Roche Diagnostics K. K. (Japan)), a substrate for measuring lipase activity, was weighed and placed in each of 24 beakers (the volume: 10 mL).

(2) Next, 2.0 g of each of the following 12 kinds (c) to (n) of a surfactant (each was a nonionic surfactant) was weighed and added to one of the different beakers used in the above (1). In addition, 4.0 g of each of the following 12 kinds (c) to (n) of a surfactant (each was a nonionic surfactant) was weighed and added to one of the different beakers used in the above (1).

(c) NIKKOL BT-7 (polyoxyethylene (7) secondary alkyl ether) (the distributor: Nikko Chemicals Co., Ltd. (Japan))

(d) NIKKOL NP-7.5 (polyoxyethylene (7.5) nonylphenyl ether) (the distributor: Nikko Chemicals Co., Ltd. (Japan))

(e) EMALGEN 1108 (polyoxyethylene (8) alkyl ether) (the distributor: Kao Corporation (Japan))

(f) Triton X-100 (polyoxyethylene (10) octylphenyl ether) (the distributor: Wako Pure Chemical Industries, Ltd. (Japan))

(g) Brij 35 (polyoxyethylene (23) lauryl ether) (the distributor: Wako Pure Chemical Industries, Ltd. (Japan))

(h) Triton X-405 (polyoxyethylene (40) isooctylphenyl ether) (the distributor: Sigma-Aldrich Co. LLC. (Japan))

(i) Tween 20 (polyoxyethylene (20) sorbitan monolaurate) (the distributor: Wako Pure Chemical Industries, Ltd. (Japan))

(j) NIKKOL NP-15 (polyoxyethylene (15) nonylphenyl ether) (the distributor: Nikko Chemicals Co., Ltd. (Japan))

(k) EMALGEN B-66 (polyoxyethylene tribenzylphenyl ether) (the distributor: Kao Corporation (Japan))

(l) EMALGEN A-60 (polyoxyethylene distyrenated phenyl ether) (the distributor: Kao Corporation (Japan))

(m) Triton X-114 (polyoxyethylene (8) octylphenyl ether) (the distributor: Wako Pure Chemical Industries, Ltd. (Japan))

(n) SANNIX GP-440 (polyoxypropylene glyceryl ether) (the manufacturer: Sanyo Chemical Industries, Ltd. (Japan))

(3) After the addition as described in the above (2), each beaker was stirred at room temperature (25° C.), and the substrate (DGGMR) for measuring lipase activity and each surfactant were mixed in each beaker.

This mixing (stirring) was performed for 5 minutes to prepare a "mixture of the substrate (DGGMR) for measuring lipase activity and each surfactant".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

(4) Next, a micropipette was used to add a "certain quantity (4.0 mL) of pure water" at room temperature (25° C.) under stirring to (all) the "mixture of the substrate (DGGMR) for measuring lipase activity and each surfactant" in the beaker as described in the above (3).

After the addition, this stirring was continued at room temperature (25° C.) for 5 minutes. In this way, the "certain quantity (4.0 mL) of pure water" was mixed with (all) the "mixture prepared by mixing the substrate (DGGMR) for measuring lipase activity and each substrate".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

(5) Next, the "mixed liquid after the mixture (the mixture of the substrate (DGGMR) for measuring lipase activity and each surfactant) and the certain quantity of pure water had been mixed" as described in the above (4) was further mixed with a certain quantity of pure water to have a final volume of 200 mL.

(6) The above procedure allowed for production of all the following 24 kinds [5] to [28] of the substrate solution for measuring lipase activity in accordance with the control process.

Note that in any of (all the 24 kinds of) these substrate solutions for measuring lipase activity, the substrate (DGGMR) for measuring lipase activity had a concentration of 0.6 mM.

Meanwhile, the concentration of each surfactant was 1.0% (w/v) in the substrate solution for measuring lipase activity obtained by weighing 2.0 g of the surfactant and adding it to the beaker as described in the above (2). Then, the concentration of the present polymer was 2.0% (w/v) in the substrate solution for measuring lipase activity obtained by weighing 4.0 g of the surfactant and adding it to the beaker.

[5] Substrate solution [5] for measuring lipase activity (the substrate for measuring lipase activity: DGGMR; the surfactant: NIKKOL BT-7 (the concentration: 1.0% (w/v)))

[6] Substrate solution [6] for measuring lipase activity (the substrate for measuring lipase activity: DGGMR; the surfactant: NIKKOL BT-7 (the concentration: 2.0% (w/v)))

[7] Substrate solution [7] for measuring lipase activity (the substrate for measuring lipase activity: DGGMR; the surfactant: NIKKOL NP-7.5 (the concentration: 1.0% (w/v)))

[8] Substrate solution [8] for measuring lipase activity (the substrate for measuring lipase activity: DGGMR; the surfactant: NIKKOL NP-7.5 (the concentration: 2.0% (w/v)))

[9] Substrate solution [9] for measuring lipase activity (the substrate for measuring lipase activity: DGGMR; the surfactant: EMALGEN 1108 (the concentration: 1.0% (w/v)))

[10] Substrate solution [10] for measuring lipase activity (the substrate for measuring lipase activity: DGGMR; the surfactant: EMALGEN 1108 (the concentration: 2.0% (w/v)))

[11] Substrate solution [11] for measuring lipase activity (the substrate for measuring lipase activity: DGGMR; the surfactant: Triton X-100 (the concentration: 1.0% (w/v)))

[12] Substrate solution [12] for measuring lipase activity (the substrate for measuring lipase activity: DGGMR; the surfactant: Triton X-100 (the concentration: 2.0% (w/v)))

[13] Substrate solution [13] for measuring lipase activity (the substrate for measuring lipase activity: DGGMR; the surfactant: Brij 35 (the concentration: 1.0% (w/v)))

[14] Substrate solution [14] for measuring lipase activity (the substrate for measuring lipase activity: DGGMR; the surfactant: Brij 35 (the concentration: 2.0% (w/v)))

[15] Substrate solution [15] for measuring lipase activity (the substrate for measuring lipase activity: DGGMR; the surfactant: Triton X-405 (the concentration: 1.0% (w/v)))

[16] Substrate solution [16] for measuring lipase activity (the substrate for measuring lipase activity: DGGMR; the surfactant: Triton X-405 (the concentration: 2.0% (w/v)))

[17] Substrate solution [17] for measuring lipase activity (the substrate for measuring lipase activity: DGGMR; the surfactant: Tween 20 (the concentration: 1.0% (w/v)))

[18] Substrate solution [18] for measuring lipase activity (the substrate for measuring lipase activity: DGGMR; the surfactant: Tween 20 (the concentration: 2.0% (w/v)))

[19] Substrate solution [19] for measuring lipase activity (the substrate for measuring lipase activity: DGGMR; the surfactant: NIKKOL NP-15 (the concentration: 1.0% (w/v)))

[20] Substrate solution [20] for measuring lipase activity (the substrate for measuring lipase activity: DGGMR; the surfactant: NIKKOL NP-15 (the concentration: 2.0% (w/v)))

[21] Substrate solution [21] for measuring lipase activity (the substrate for measuring lipase activity: DGGMR; the surfactant: EMALGEN B-66 (the concentration: 1.0% (w/v)))

[22] Substrate solution [22] for measuring lipase activity (the substrate for measuring lipase activity: DGGMR; the surfactant: EMALGEN B-66 (the concentration: 2.0% (w/v)))

[23] Substrate solution [23] for measuring lipase activity (the substrate for measuring lipase activity: DGGMR; the surfactant: EMALGEN A-60 (the concentration: 1.0% (w/v)))

[24] Substrate solution [24] for measuring lipase activity (the substrate for measuring lipase activity: DGGMR; the surfactant: EMALGEN A-60 (the concentration: 2.0% (w/v)))

[25] Substrate solution [25] for measuring lipase activity (the substrate for measuring lipase activity: DGGMR; the surfactant: Triton X-114 (the concentration: 1.0% (w/v)))

[26] Substrate solution [26] for measuring lipase activity (the substrate for measuring lipase activity: DGGMR; the surfactant: Triton X-114 (the concentration: 2.0% (w/v)))

[27] Substrate solution [27] for measuring lipase activity (the substrate for measuring lipase activity: DGGMR; the surfactant: SANNIX GP-440 (the concentration: 1.0% (w/v)))

[28] Substrate solution [28] for measuring lipase activity (the substrate for measuring lipase activity: DGGMR; the surfactant: SANNIX GP-440 (the concentration: 2.0% (w/v)))

2. Observation of Substrate Solution for Measuring Lipase Activity and Measuring Diameter of Micelles in Emulsion Thereof <1> Observation of Substrate Solution for Measuring Lipase Activity (1) Inspection With respect to the 4 kinds ([1] to [4] of the above section 1.<1>(7)) of the substrate solution for measuring lipase activity produced by the process of the present invention and the 24 kinds ([5] to [28] of the above section 1.<2>(7)) of the substrate solution for measuring lipase activity produced by the control process, each was visually inspected.

(2) Observation Results

Table 3 shows the observation results of the substrate solutions for measuring lipase activity that had been visually inspected in the above (1).

Note that in the column "Observation Results" in this table, "○" indicates that "neither a concentration gradient, strong turbidity, nor coloring was observed". In addition, the "×(*3)" indicate "not uniform (the substrate for measuring lipase activity and each surfactant were separated or were separated into an oil layer and a water layer)".

TABLE 3

| Substrate Solution for Measuring Lipase Activity | | Concentration (% (w/v)) | Observation Results | (Averaged) Diameter (Particle Size) of Micelles in Emulsion |
|---|---|---|---|---|
| Present Invention | | | | |
| | Present Polymer | | | |
| Substrate Solution (1) for Measuring Lipase Activity | KF-351A | 1.0 | ○ | 170 nm |
| Substrate Solution (2) for Measuring Lipase Activity | KF-351A | 2.0 | ○ | 177 nm |
| Substrate Solution (3) for Measuring Lipase Activity | KF-6011 | 1.0 | ○ | 180 nm |
| Substrate Solution (4) for Measuring Lipase Activity | KF-6011 | 2.0 | ○ | 160 nm |
| Control | | | | |
| | Surfactant | | | |
| Substrate Solution (5) for Measuring Lipase Activity | NIKKOL BT-7 | 1.0 | ○ | [Less than 10 nm] |
| Substrate Solution (6) for Measuring Lipase Activity | NIKKOL BT-7 | 2.0 | ○ | [Less than 10 nm] |
| Substrate Solution (7) for Measuring Lipase Activity | NIKKOL NP-7.5 | 1.0 | ○ | [Less than 10 nm] |
| Substrate Solution (8) for Measuring Lipase Activity | NIKKOL NP-7.5 | 2.0 | ○ | [Less than 10 nm] |
| Substrate Solution (9) for Measuring Lipase Activity | EMALGEN 1108 | 1.0 | ○ | [Less than 10 nm] |
| Substrate Solution (10) for Measuring Lipase Activity | EMALGEN 1108 | 2.0 | ○ | [Less than 10 nm] |
| Substrate Solution (11) for Measuring Lipase Activity | Triton X-100 | 1.0 | ○ | [Less than 10 nm] |
| Substrate Solution (12) for Measuring Lipase Activity | Triton X-100 | 2.0 | ○ | [Less than 10 nm] |
| Substrate Solution (13) for Measuring Lipase Activity | Brij35 | 1.0 | ○ | [Less than 10 nm] |
| Substrate Solution (14) for Measuring Lipase Activity | Brij35 | 2.0 | ○ | [Less than 10 nm] |
| Substrate Solution (15) for Measuring Lipase Activity | Triton X-405 | 1.0 | x (*3) | (Not measured) |
| Substrate Solution (16) for Measuring Lipase Activity | Triton X-405 | 2.0 | x (*3) | (Not measured) |
| Substrate Solution (17) for Measuring Lipase Activity | Tween20 | 1.0 | ○ | [Less than 10 nm] |
| Substrate Solution (18) for Measuring Lipase Activity | Tween20 | 2.0 | ○ | [Less than 10 nm] |
| Substrate Solution (19) for Measuring Lipase Activity | NIKKOL NP-15 | 1.0 | ○ | [Less than 10 nm] |
| Substrate Solution (20) for Measuring Lipase Activity | NIKKOL NP-15 | 2.0 | ○ | [Less than 10 nm] |
| Substrate Solution (21) for Measuring Lipase Activity | EMALGEN B-66 | 1.0 | x (*3) | (Not measured) |
| Substrate Solution (22) for Measuring Lipase Activity | EMALGEN B-66 | 2.0 | x (*3) | (Not measured) |
| Substrate Solution (23) for Measuring Lipase Activity | EMALGEN A-60 | 1.0 | ○ | [Less than 10 nm] |
| Substrate Solution (24) for Measuring Lipase Activity | EMALGEN A-60 | 2.0 | ○ | [Less than 10 nm] |
| Substrate Solution (25) for Measuring Lipase Activity | Triton X-114 | 1.0 | ○ | [Less than 10 nm] |
| Substrate Solution (26) for Measuring Lipase Activity | Triton X-114 | 2.0 | ○ | [Less than 10 nm] |
| Substrate Solution (27) for Measuring Lipase Activity | SANNIX GP-440 | 1.0 | x (*3) | (Not measured) |
| Substrate Solution (28) for Measuring Lipase Activity | SANNIX GP-440 | 2.0 | x (*3) | (Not measured) |

Observation results

○: neither a concentration gradient, strong turbidity, nor coloring was observed.

x (*3): not uniform (the substrate for measuring lipase activity and each surfactant were separated or were separated into an oil layer and a water layer).

<2> Measuring Diameter of Micelles in Emulsion of Substrate Solution for Measuring Lipase Activity With respect to the 4 kinds ([1] to [4] of the above section 1.<1>(7)) of the substrate solution for measuring lipase activity produced by the process of the present invention and the 18 kinds ([5] to [14], [17] to [20], and [23] to [26] of the above section 1.<2>(7)) of the substrate solution for measuring lipase activity produced by the control process, the diameter of micelles in each emulsion was measured.

Note that Table 3, which have showed the observation results, demonstrates that each of the 6 kinds of the substrate solution for measuring lipase activity ([15], [16], [21], [22], [27], and [28] of the above section 1.<2>(7)) produced by the control process was "not uniform" (the substrate for measuring lipase activity and each surfactant were separated or were separated into an oil layer and a water layer)". It was obvious that they were unsuited for measuring lipase activity, so that the diameter of micelles in each emulsion was not measured.

(1) Measuring Diameter of Micelles in Emulsion

With respect to the 4 kinds ([1] to [4] of the above section 1.<1>(7)) of the substrate solution for measuring lipase activity produced by the process of the present invention and the 18 kinds ([5] to [14], [17] to [20], and [23] to [26] of the above section 1.<2>(7)) of the substrate solution for measuring lipase activity produced by the control process, the diameter (particle size) of micelles in an emulsion of each substrate solution for measuring lipase activity was measured while the procedure was executed as described in the section 2.(1)(i) to (ii) of Example 2.

(2) Measured Results

Table 3 shows the diameter (particle size) of micelles in an emulsion of each substrate solution for measuring lipase activity as measured in the above (1).

Note that Table 3 indicates the averaged diameter (particle size) of micelles in an emulsion of each substrate solution for measuring lipase activity.

Here, the column "Diameter (Particle Size) of Micelles in Emulsion" in this table shows measured values of the diameter (particle size) of micelles in an emulsion of each substrate solution for measuring lipase activity. In the dynamic light-scattering particle size distribution analyzer (the model: Nanotrac UPA-EX250) used for the measurement, the lower limit of measurement with respect to the diameter (particle size) of micelles is 10 nm. Accordingly, when the analyzer displayed that the measured result was less than the lower limit of measurement, the corresponding space was filled in with "Less than 10 nm".

3. Discussion

<1> Substrate Solution for Measuring Lipase Activity Produced by Process of the Present Invention Table 3 demonstrates that there was neither an observable concentration gradient, strong turbidity, nor coloring in any of the 4 kinds of the substrate solution for measuring lipase activity (substrate solutions (1) to (4) for measuring lipase activity) produced in accordance with the production process and the production-simplifying method according to the present invention. Hence, no such problems were found.

In addition, Table 3 demonstrates that regarding the 4 kinds of the substrate solution for measuring lipase activity (i.e., the substrate solutions (1) to (4) for measuring lipase activity) produced in accordance with the production process and the production-simplifying method according to the present invention, the diameter (particle size) of micelles in each emulsion ranges from 100 nm to 200 nm.

That is, the diameter (particle size) of micelles was measured as described above. The results demonstrate that any of the four kinds of the substrate solution for measuring lipase activity is composed of micelle particles and is produced as an emulsified substrate solution for measuring lipase activity.

In any of these 4 kinds of the substrate solution for measuring lipase activity, the diameter (particle size) of micelles in each emulsion is found to be within a range from 60 nm to 1,500 nm, in which range the rate of reaction with a lipase is high, the resulting emulsion is stable, and the substrate solution for measuring lipase activity can be stored and used for a long period.

The above has confirmed that the process for producing a substrate solution for measuring lipase activity according to the present invention, the method for simplifying production of a substrate solution for measuring lipase activity according to the present invention, and the substrate solutions as produced in accordance with the process and the method are characterized by the following points (i) to (iii).

(i) In conventional processes, a substrate for measuring lipase activity is mixed into a solution containing an organic solvent (e.g., an alcohol); a liquid containing a substrate for measuring lipase activity is added dropwise and mixed into a solution; a liquid containing a substrate for measuring lipase activity is jet-injected into a solution; a substrate solution for measuring lipase activity is stirred using a strong mixer at a high speed; a substrate solution for measuring lipase activity is subjected to ultrasonication; or the like. In the present invention, the mixing does not necessitate cumbersome or special processing such that skill is required, or does not necessitate a special apparatus or other items.

(ii) The substrate solution for measuring lipase activity can be stirred, for example, using a common mixer at a typical speed, and can thus be produced using a simple, short, and inexpensive procedure. Hence, the production of the substrate solution for measuring lipase activity can be simplified.

(iii) The substrate solution for measuring lipase activity produced is suitable for the measurement of lipase activity in a sample.

<2> Substrate Solution for Measuring Lipase Activity Produced by Control Process Table 3 demonstrates that each of the 6 kinds of the substrate solution for measuring lipase activity ([15], [16], [21], [22], [27], and [28] of the above section 1.<2>(7)) produced by the control process was "not uniform" (the substrate for measuring lipase activity and each surfactant were separated or were separated into an oil layer and a water layer)", and is unsuitable for measuring lipase activity.

In addition, Table 3 shows the measurement results in which regarding the 18 kinds of the substrate solution ([5] to [14], [17] to [20], and [23] to [26] of the above section 1.<2>(7)) for measuring lipase activity produced by the control process, the diameter (particle size) of micelles in each emulsion was less than the lower limit of measurement, namely, "less than 10 nm", indicating that none of them was produced as an emulsified substrate solution for measuring lipase activity that was composed of micelle particles.

Hence, any of (the total of 24 kinds of) these substrate solutions for measuring lipase activity produced by the control process is found to be unsuitable for measuring lipase activity in a sample.

Example 4

(Measuring Lipase Activity in Sample)

Lipase activity in a sample was measured using each substrate solution for measuring lipase activity produced by the process of the present invention.

1. Measuring Reagent

<1> Measuring Reagent Containing Substrate Solution for Measuring Lipase Activity Produced by Process of the Present Invention A reagent for measuring lipase activity (reagent kit for measuring lipase activity) was produced that was composed of a second reagent and a first reagent corresponding to the second reagent composed of each substrate solution for measuring lipase activity produced by the process for producing a substrate solution for measuring lipase activity and the method for simplifying production of the substrate solution according to the present invention.

(1) First Reagent

The following reagent components were each dissolved at the designated concentration into pure water, and the pH was adjusted to pH 8.4 (20° C.) to prepare the first reagent.

Sodium deoxycholate (a lipase promoter) 2% (w/v)
Calcium chloride (a lipase activator) 5 mM
Colipase (derived from a pig pancreas; the distributor: Roche Diagnostics K. K. (Japan)) 375K Unit/L (5 mg/L)
Bicine (a buffer) 40 mM (2) Second Reagent The 6 kinds ((a) to (f) of the section 2.(7) of Example 1) of the substrate solution for measuring lipase activity (the substrate (DGGMR) for measuring lipase activity had a concentration of 0.6 mM; the present polymer had a concentration of 2.0% (w/v)) produced by the process of the present invention (described below) were each used as the second reagent.

(a) Substrate solution (a) for measuring lipase activity (the substrate for measuring lipase activity: DGGMR; the present polymer: KF-351A)

(b) Substrate solution (b) for measuring lipase activity (the substrate for measuring lipase activity: DGGMR; the present polymer: KF-354L)

(c) Substrate solution (c) for measuring lipase activity (the substrate for measuring lipase activity: DGGMR; the present polymer: KF-355A)

(d) Substrate solution (d) for measuring lipase activity (the substrate for measuring lipase activity: DGGMR; the present polymer: KF-6011)

(e) Substrate solution (e) for measuring lipase activity (the substrate for measuring lipase activity: DGGMR; the present polymer: Pluronic L-34)

(f) Substrate solution (f) for measuring lipase activity (the substrate for measuring lipase activity: DGGMR; the present polymer: Pluronic L-44)

<2> Commercially Available Control Reagent

A commercially available reagent for measuring lipase activity (reagent kit for measuring lipase activity) "Liquitech Lipase Color II" (the distributor: Roche Diagnostics K. K. (Japan)) was used as a control.

Note that this "Liquitech Lipase Color II" (hereinafter, sometimes referred to as a "commercially available control reagent") is composed of a "buffer", which is the first reagent, and a "substrate liquid", which is the second reagent, (containing DGGMR as a substrate for measuring lipase activity).

2. Sample

The following "(1) reference material", "(2) control serum-1", "(3) control serum-2", and "(4) control serum-3" were each used as a sample.

(1) Reference Material

A commercially available reference material, a "Reference Standard-JSCC Enzyme, (JCCLS CRM-001)" (Lot No. 001b; the distributor: Reference Material Institute for Clinical Chemistry Standards (Japan)) was used as the "reference material".

(2) Control Serum-1

The "Aalto Control I G" (the distributor: Shino-Test Corporation (Japan)) of commercially available control serum for quality control was used as the "control serum-1".

(3) Control Serum-2

A "prototype" of the "Aalto Control II" (Shino-Test Corporation (Japan)) of control serum for quality control was used as the "control serum-2".

(4) Control Serum-3

The "Aalto Control CRPII U" (the distributor: Shino-Test Corporation (Japan)) of commercially available control serum for quality control was used as the "control serum-3".

3. Measuring Lipase Activity in Sample

Lipase activity in each sample of the above section 2 was measured as described below.

<1> Measurement Using Measuring Reagent Containing Substrate Solution for Measuring Lipase Activity Produced by Process of the Present Invention A reagent for measuring lipase activity (reagent kit for measuring lipase activity) was composed of the second reagent and the first reagent corresponding to the second reagent containing the substrate solution for measuring lipase activity produced by the process of the present invention, and was used for measuring lipase activity in each sample of the above section 2 by using a 7180 clinical analyzer (the distributor: Hitachi High-Technologies Corporation (Japan)).

(1) Case where Substrate Solution (a) for Measuring Lipase Activity was Used as Second Reagent (a) In the 7180 clinical analyzer, 160 µL of the "first reagent" of the section 1.<1>(1) was added as the first reagent to 2.6 µL of each of the samples including the "(1) reference material", "(2) control serum-1", "(3) control serum-2", and "(4) control serum-3" as described in the above section 2 to make a reaction at 37° C.

(b) Next, between point 16 (270.093 seconds after addition of the first reagent) and point 17 (286.977 seconds after addition of the first reagent) was added, as the second reagent, 96 µL of the "substrate solution (a) for measuring lipase activity" of the above section 1.<1>(2)(a) to make a reaction at 37° C.

(c) Then, a change in absorbance from point 30 (516.049 seconds after addition of the first reagent) to point 34 (587.426 seconds after addition of the first reagent) was measured at a main wavelength of 570 nm and another wavelength of 700 nm (based on an increase in concentration of 6'-methylresorufin generated in response to lipase activity value in a sample, a change in absorbance was measured).

(d) Note that as a calibrator for calibration, a "calibrator II (C.f.a.s. II) for automated analysis" (Lot No. 158688; the distributor: Roche Diagnostics K. K. (Japan)) was used.

The same procedure as described in the above (a) to (c) was performed except that the "calibrator II (C.f.a.s. for automated analysis" was used as a sample. Then, a change in absorbance when the calibrator "calibrator II (C.f.a.s. II) for automated analysis" was used for measurement was determined (based on an increase in concentration of 6'-methylresorufin generated in response to lipase activity value (known value) in the calibrator, a change in absorbance was measured).

(e) Meanwhile, saline was used for measurement of a blank reagent.

The same procedure as described in the above (a) to (c) was performed except that the saline was used as a sample. Then, a change in absorbance when the saline was used for measurement was determined (a change in absorbance of the blank reagent was measured).

(f) Next, a "value of difference in change in absorbance of each sample" was calculated by subtracting the change in absorbance of the blank reagent between the above points, which change had been calculated in the above (e), from the change in absorbance of each sample of the above section 2 between the above points, which change had been calculated in the above (c).

In addition, a "value of difference in change in absorbance of the calibrator" was calculated by subtracting the change in absorbance of the blank reagent between the above points, which change had been calculated in the above (e), from the change in absorbance of the calibrator (with a known lipase activity value) between the above points, which change had been calculated in the above (d).

Subsequently, the "value of difference in change in absorbance of each sample", the "value of difference in change in absorbance of the calibrator", and the known "lipase activity value of the calibrator" were compared. Then, the proportion was calculated to give the lipase activity value of each sample as described in the section 2.

(2) Case where Substrate Solution (b) for Measuring Lipase Activity was Used as Second Reagent The same procedure as described in the above (1)(a) to (f) was performed except that the substrate solution (b) (of the above section 1.<1>(2)(b)) for measuring lipase activity instead of the substrate solution (a) for measuring lipase activity was used as the second reagent of the above (1)(b); and the points (point timings) at which a change in absorbance was measured as described in the above (1)(c) were switched from "between points 30 and 34" to "between point 24 (411.887 seconds after addition of the first reagent) and point 28 (480.360 seconds after addition of the first reagent). Then, the lipase activity value of each sample of the above section 2 when the substrate solution (b) for measuring lipase activity was used as the second reagent was determined.

(3) Case where Substrate Solution (c) for Measuring Lipase Activity was Used as Second Reagent The same procedure as described in the above (1)(a) to (f) was performed except that the substrate solution (c) (of the above section 1.<1>(2)(c)) for measuring lipase activity instead of the substrate solution (a) for measuring lipase activity was used as the second reagent of the above (1)(b). Then, the lipase activity value of each sample of the above section 2 when the substrate solution (c) for measuring lipase activity was used as the second reagent was determined.

(4) Case where Substrate Solution (d) for Measuring Lipase Activity was Used as Second Reagent The same procedure as described in the above (1)(a) to (f) was performed except that the substrate solution (d) (of the above section 1.<1>(2)(d)) for measuring lipase activity instead of the substrate solution (a) for measuring lipase activity was used as the second reagent of the above (1)(b). Then, the lipase activity value of each sample of the above section 2 when the substrate solution (d) for measuring lipase activity was used as the second reagent was determined.

(5) Case where Substrate Solution (e) for Measuring Lipase Activity was Used as Second Reagent The same procedure as described in the above (1)(a) to (f) was performed except that the substrate solution (e) (of the above section 1.<1>(2)(e)) for measuring lipase activity instead of the substrate solution (a) for measuring lipase activity was used as the second reagent of the above (1)(b); and the points (point timings) at which a change in absorbance was measured as described in the above (1)(c) were switched from "between points 30 and 34" to "between point 23 (394.043 seconds after addition of the first reagent) and point 27 (462.516 seconds after addition of the first reagent). Then, the lipase activity value of each sample of the above section 2 when the substrate solution (e) for measuring lipase activity was used as the second reagent was determined.

(6) Case where Substrate Solution (f) for Measuring Lipase Activity was Used as Second Reagent The same procedure as described in the above (1)(a) to (f) was performed except that the substrate solution (f) (of the above section 1.<1>(2)(f)) for measuring lipase activity instead of the substrate solution (a) for measuring lipase activity was used as the second reagent of the above (1)(b); and the points (point timings) at which a change in absorbance was measured as described in the above (1)(c) were switched from "between points 30 and 34" to "between point 19 (322.665 seconds after addition of the first reagent) and point 23 (394.043 seconds after addition of the first reagent). Then, the lipase activity value of each sample of the above section 2 when the substrate solution (f) for measuring lipase activity was used as the second reagent was determined.

<2> Measurement Using Commercially Available Control Reagent

A commercially available control reagent was used for measuring lipase activity in each sample of the above section 2 by using a 7180 clinical analyzer (the distributor: Hitachi High-Technologies Corporation (Japan)).

Specifically, the same procedure as described in the above <1>(1)(a) to (f) was performed except that the "buffer" of the "commercially available control reagent" (of the above section 1.<2>) instead of the "first reagent" was used as the first reagent as described in the above <1>(1)(a); the "substrate solution" of the "commercially available control reagent" (of the above section 1.<2>) instead of the substrate solution (a) for measuring lipase activity was used as the second reagent of the above <1>(1)(b); and the points (point timings) at which a change in absorbance was measured as described in the above <1>(1)(c) were switched from "between points 30 and 34" to "between point 21 (358.354 seconds after addition of the first reagent) and point 25 (429.732 seconds after addition of the first reagent). Then, the lipase activity value of each sample of the above section 2 when the commercially available control reagent was used was determined.

(4) Measurement Results

The measurement was carried out as described in the above section 3.<1> and <2>. Table 4 shows the measured lipase activity value of each sample as described in the above section 2.

Note that the lipase activity value of each sample shown in Table 4 is represented in Unit/L.

TABLE 4

|  | Substrate Solution for Measuring Lipase Activity | Present Polymer | Measured Values | | | |
|---|---|---|---|---|---|---|
|  |  |  | Standard Material | Control Serum-1 | Control Serum-2 | Control Serum-3 |
| Present Invention | Substrate Solution (a) for Measuring Lipase Activity | KF-351A | 167.0 | 24.6 | 27.2 | 29.6 |
|  | Substrate Solution (b) for Measuring Lipase Activity | KF-354L | 164.6 | 20.8 | 23.2 | 25.7 |
|  | Substrate Solution (c) for Measuring Lipase Activity | KF-355A | 146.3 | 24.0 | 25.0 | 30.9 |
|  | Substrate Solution (d) for Measuring Lipase Activity | KF-6011 | 149.5 | 25.7 | 28.2 | 32.8 |
|  | Substrate Solution (e) for Measuring Lipase Activity | Pluronic L-34 | 178.3 | 21.8 | 23.2 | 25.9 |
|  | Substrate Solution (f) for Measuring Lipase Activity | Pluronic L-44 | 157.7 | 21.5 | 22.3 | 26.0 |
| Commercially Available Control Reagent |  |  | 143.1 | 22.4 | 25.6 | 27.9 |

[Unit/L]

5. Discussion

In Table 4, the substrate solutions for measuring lipase activity produced by the process of the present invention were used to obtain the measurement results (measured values) of the lipase activity value in each sample. Even when the six kinds of the substrate solution for measuring lipase activity (the substrate solutions (a to f) for measuring lipase activity) were used, any of them gave substantially the same values as the measurement results (measured values) of the lipase activity value as calculated using the commercially available control reagent.

This demonstrates that the substrate solutions for measuring lipase activity produced in accordance with the process for producing a substrate solution for measuring lipase activity and the method for simplifying production of a substrate solution for measuring lipase activity according to the present invention can be used to accurately measure lipase activity in a sample.

Specifically, when the process for producing a substrate solution for measuring lipase activity and the method for simplifying production of a substrate solution for measuring lipase activity according to the present invention are used, the production of the substrate solution for measuring lipase activity can be made simple, less time-consuming, and low-cost. Besides, it has been demonstrated that the substrate solutions can provide accurate measurement results (measured values) of lipase activity in a sample.

Example 5

(Correlation Between Measurements of Lipase Activity in Sample)

Lipase activity in a sample was measured using each substrate solution for measuring lipase activity produced by the process of the present invention. Also, lipase activity in the same sample was measured using the commercially available control reagent. Then, the correlation between these results were examined.

1. Measuring Reagent

<1> Measuring Reagent Containing Substrate Solution for Measuring Lipase Activity Produced by Process of the Present Invention A reagent for measuring lipase activity (reagent kit for measuring lipase activity) was used that was composed of a second reagent and a first reagent corresponding to the second reagent containing each substrate solution for measuring lipase activity produced by the process for producing a substrate solution for measuring lipase activity and the method for simplifying production of the substrate solution according to the present invention.

[1] First Reagent

As the first reagent, the "first reagent" as described in the section 1.<1>(1) of Example 4 was used.

[2] Second Reagent

A substrate solution for measuring lipase activity was produced in accordance with the process for producing a substrate solution for measuring lipase activity and the method for simplifying production of the substrate solution according to the present invention.

(1) First, 0.09 g of 1,2-o-dilauryl-rac-glycero-3-glutaric acid (6'-methylresorufin) ester (DGGMR) (the distributor: Roche Diagnostics K. K. (Japan)), a substrate for measuring lipase activity according to the present invention, was weighed and placed in each of 5 beakers (the volume: 10 mL).

(2) Next, 4.0 g of each of the following 3 kinds (a) to (c) of the side-chain-type nonreactive modified silicone oil (polyether modified type) and the following 2 kinds (d) to (e) of the polyoxyethylene/polyoxypropylene condensate was weighed and added to one of the different beakers used in the above (1).

(a) KF-351A (the distributor: Shin-Etsu Chemical Co., Ltd. (Japan))

(b) KF-354L (the distributor: Shin-Etsu Chemical Co., Ltd. (Japan))

(c) KF-355A (the distributor: Shin-Etsu Chemical Co., Ltd. (Japan))

(d) Pluronic L-34 (the distributor: ADEKA CORPORATION (Japan))

(e) Pluronic L-44 (the distributor: ADEKA CORPORATION (Japan))

(3) After the addition as described in the above (2), each beaker was placed in a thermostat water tank (model: BK-33; the distributor; YAMATO SCIENTIFIC CO., LTD. (Japan)) set at a temperature of 67° C. Then, each beaker was stirred and the substrate (DGGMR) for measuring lipase activity and the present polymer were mixed at 67° C. Note that the temperature of the water tank was measured and checked with a mercury thermometer.

This mixing (stirring) at 67° C. was performed for 5 minutes to prepare a "mixture of the substrate (DGGMR) for measuring lipase activity and the present polymer".

Note that each beaker was placed on a stirrer (a remote-driven electromagnetic stirrer; the model: HP40107; the distributor: Sansho Co., Ltd. (Japan)) in the water tank at a temperature of 67° while this stirring was performed. A magnet bar in each beaker was rotated while the dial of a control unit of this stirrer was set to "3".

(4) Next, all of the "mixture of the substrate (DGGMR) for measuring lipase activity and the present polymer" as described in the above (3) was aspirated using a micropipette from each beaker. All (all the amount) of the mixture was added from the micropipette to a "certain quantity (4.0 mL) of pure water", which had been kept at 20° C. in another beaker (the volume: 10 mL), under stirring.

After the addition, this stirring was continued at room temperature (25° C.) for 5 minutes. In this way, the "certain quantity (4.0 mL) of pure water" was mixed with (all) the mixture prepared by mixing the substrate (DGGMR) for measuring lipase activity and the present polymer".

Note that each beaker was placed on a multi-stirrer (the model: M-3; the distributor: AS ONE Corporation (Japan)) while this stirring was performed. A magnet bar in each beaker was rotated while the dial of a control unit of this multi-stirrer was set to "3".

Meanwhile, the temperature of the "certain quantity (4.0 mL) of pure water" in each beaker was measured with a mercury thermometer, and whether or not the temperature was 20° C. was checked.

(5) Next, the "mixed liquid after the mixture (the mixture of the substrate (DGGMR) for measuring lipase activity and the present polymer) and the certain quantity of pure water had been mixed" as described in the above (4) was further mixed with a certain quantity of pure water to have a final volume of 200 mL.

(6) The above procedure allowed for production of all the following five kinds (i) to (v) of the substrate solution for measuring lipase activity in accordance with the production process and the production-simplifying method according to the present invention.

Note that in any of (all the 5 kinds of) these substrate solutions for measuring lipase activity, the substrate (DGGMR) for measuring lipase activity had a concentration of 0.6 mM and the present polymer had a concentration of 2.0% (w/v).

In addition, there was neither an observable concentration gradient nor strong turbidity in any of (all the five kinds of) these substrate solutions for measuring lipase activity. In this way, whether or not each substrate solution was mixed uniformly was visually inspected.

(i) Substrate solution (i) for measuring lipase activity (the substrate for measuring lipase activity: DGGMR; the present polymer: KF-351A)

(ii) Substrate solution (ii) for measuring lipase activity (the substrate for measuring lipase activity: DGGMR; the present polymer: KF-354L)

(iii) Substrate solution (iii) for measuring lipase activity (the substrate for measuring lipase activity: DGGMR; the present polymer: KF-355A)

(iv) Substrate solution (iv) for measuring lipase activity (the substrate for measuring lipase activity: DGGMR; the present polymer: Pluronic L-34)

(v) Substrate solution (v) for measuring lipase activity (the substrate for measuring lipase activity: DGGMR; the present polymer: Pluronic L-44)

<2> Commercially Available Control Reagent

A commercially available reagent for measuring lipase activity (reagent kit for measuring lipase activity) "Liquitech Lipase Color II" (the distributor: Roche Diagnostics K. K. (Japan)) as described in the section 1.<2> of Example 4 was used as a commercially available control reagent.

2. Sample

The following "(1) reference material", "(2) control serum-1", "(3) control serum-2", "(4) control serum-3", "(5) pooled serum", and "(6) human serum" were each used as a sample.

(1) Reference Material

A commercially available reference material, a "Reference Standard-JSCC Enzyme, (JCCLS CRM-001)" (Lot No. 001b; the distributor: Reference Material Institute for Clinical Chemistry Standards (Japan)) was used as the "reference material".

(2) Control Serum-1

The "Aalto Control I G" (the distributor: Shino-Test Corporation (Japan)) of commercially available control serum for quality control was used as the "control serum-1".

(3) Control Serum-2

A "prototype" of the "Aalto Control II" (Shino-Test Corporation (Japan)) of control serum for quality control was used as the "control serum-2".

(4) Control Serum-3

The "Aalto Control CRPII U" (the distributor: Shino-Test Corporation (Japan)) of commercially available control serum for quality control was used as the "control serum-3".

(5) Pooled Serum

A mixture of human sera was used as "pooled serum".

(6) Human Serum

Human serum (the total of 50 samples) was used as "human serum".

3. Measuring Lipase Activity in Sample

Lipase activity in each sample of the above section 2 was measured as described below.

<1> Measurement Using Measuring Reagent Containing Substrate Solution for Measuring Lipase Activity Produced by Process of the Present Invention A reagent for measuring lipase activity (reagent kit for measuring lipase activity) was composed of the second reagent and the first reagent corresponding to the second reagent containing the substrate solution for measuring lipase activity produced by the process of the present invention, and was used for measuring lipase activity in each sample of the above section 2 by using a 7180 clinical analyzer (the distributor: Hitachi High-Technologies Corporation (Japan)).

(1) Case where Substrate Solution (i) for Measuring Lipase Activity was Used as Second Reagent (a) In the 7180 clinical analyzer, 160 µL of the "first reagent" of the section 1.<1>(1) was added as the first reagent to 2.6 µL of each of the samples including the "(1) reference material", "(2) control serum-1", "(3) control serum-2", "(4) control serum-3", "(5) pooled serum", and "(6) human serum" as described in the above section 2 to make a reaction at 37° C.

(b) Next, between point 16 (270.093 seconds after addition of the first reagent) and point 17 (286.977 seconds after addition of the first reagent) was added, as the second reagent, 96 µL of the "substrate solution (i) for measuring lipase activity" of the above section 1.<1>[2](7)(i) to make a reaction at 37° C.

(c) Then, a change in absorbance from point 30 (516.049 seconds after addition of the first reagent) to point 34 (587.426 seconds after addition of the first reagent) was measured at a main wavelength of 570 nm and another wavelength of 700 nm (based on an increase in concentration of 6'-methylresorufin generated in response to lipase activity value in a sample, a change in absorbance was measured).

(d) Note that as a calibrator for calibration, a "calibrator II (C.f.a.s. II) for automated analysis" (Lot No. 158688; the distributor: Roche Diagnostics K. K. (Japan)) was used.

The same procedure as described in the above (a) to (c) was performed except that the "calibrator II (C.f.a.s. for automated analysis" was used as a sample. Then, a change in absorbance when the calibrator "calibrator II (C.f.a.s. II) for automated analysis" was used for measurement was determined (based on an increase in concentration of 6'-methylresorufin generated in response to lipase activity value (known value) in the calibrator, a change in absorbance was measured).

(e) Meanwhile, saline was used for measurement of a blank reagent.

The same procedure as described in the above (a) to (c) was performed except that the saline was used as a sample. Then, a change in absorbance when the saline was used for measurement was determined (a change in absorbance of the blank reagent was measured).

(f) Next, a "value of difference in change in absorbance of each sample" was calculated by subtracting the change in absorbance of the blank reagent between the above points, which change had been calculated in the above (e), from the change in absorbance of each sample the above section 2 between the above points, which change had been calculated in the above (c).

In addition, a "value of difference in change in absorbance of the calibrator" was calculated by subtracting the change in absorbance of the blank reagent between the above points, which change had been calculated in the above (e), from the change in absorbance of the calibrator (with a known lipase activity value) between the above points, which change had been calculated in the above (d).

Subsequently, the "value of difference in change in absorbance of each sample", the "value of difference in change in absorbance of the calibrator", and the known "lipase activity value of the calibrator" were compared. Then, the proportion was calculated to give the lipase activity value of each sample as described in the section 2.

(2) Case where Substrate Solution (ii) for Measuring Lipase Activity was Used as Second Reagent The same procedure as described in the above (1)(a) to (f) was performed except that the substrate solution (ii) (of the above section 1.<1>[2](7)(ii)) for measuring lipase activity instead of the substrate solution (i) for measuring lipase activity was used as the second reagent of the above (1)(b); and the points (point timings) at which a change in absorbance was measured as described in the above (1)(c) were switched from "between points 30 and 34" to "between point 24 (411.887 seconds after addition of the first reagent) and point 28 (480.360 seconds after addition of the first reagent). Then, the lipase activity value of each sample of the above section 2 when the substrate solution (ii) for measuring lipase activity was used as the second reagent was determined.

(3) Case where Substrate Solution (iii) for Measuring Lipase Activity was Used as Second Reagent The same procedure as described in the above (1)(a) to (f) was performed except that the substrate solution (iii) (of the above section 1.<1>[2](7)(iii)) for measuring lipase activity instead of the substrate solution (i) for measuring lipase activity was used as the second reagent of the above (1)(b). Then, the lipase activity value of each sample of the above section 2 when the substrate solution (iii) for measuring lipase activity was used as the second reagent was determined.

(4) Case where Substrate Solution (iv) for Measuring Lipase Activity was Used as Second Reagent The same procedure as described in the above (1)(a) to (f) was performed except that the substrate solution (iv) (of the above section 1.<1>[2](7)(iv)) for measuring lipase activity instead of the substrate solution (i) for measuring lipase activity was used as the second reagent of the above (1)(b); and the points (point timings) at which a change in absorbance was measured as described in the above (1)(c) were switched from "between points 30 and 34" to "between point 23 (394.043 seconds after addition of the first reagent) and point 27 (462.516 seconds after addition of the first reagent). Then, the lipase activity value of each sample of the above section 2 when the substrate solution (iv) for measuring lipase activity was used as the second reagent was determined.

(5) Case where Substrate Solution (v) for Measuring Lipase Activity was Used as Second Reagent The same procedure as described in the above (1)(a) to (f) was performed except that the substrate solution (v) (of the above section 1.<1>[2](7)(v)) for measuring lipase activity instead of the substrate solution (i) for measuring lipase activity was used as the second reagent of the above (1)(b); and the points (point timings) at which a change in absorbance was measured as described in the above (1)(c) were switched from "between points 30 and 34" to "between point 19 (322.665 seconds after addition of the first reagent) and point 23 (394.043 seconds after addition of the first reagent). Then, the lipase activity value of each sample of the above section 2 when the substrate solution (v) for measuring lipase activity was used as the second reagent was determined.

<2> Measurement Using Commercially Available Control Reagent

A commercially available control reagent was used for measuring lipase activity in each sample of the above section 2 by using a 7180 clinical analyzer (the distributor: Hitachi High-Technologies Corporation (Japan)).

The procedure according to the assay described in the section 3.<2> of Example 4 was performed for measuring the lipase activity of each sample as described in the above section 2.(1) to (6) by using the "buffer" (first reagent) and the "substrate liquid" (second reagent) of the "commercially available control reagent" of the above section 1.<2>. Then, the lipase activity value of each of the corresponding samples was determined.

4. Measurement Results (1) Correlation Graphs

FIG. 1 is graphs indicating the correlation between the measurement results (measured values) of the lipase activity value of each sample of the section 3.<1> and the measurement results (measured values) of the lipase activity value of each sample of the section 3.<2>.

Note that FIG. 1 is a graph indicating the correlation when the substrate solution (i) for measuring lipase activity was used as the substrate solution for measuring lipase activity produced by the process of the present invention; FIG. 1 is a graph indicating the correlation when the substrate solution (ii) for measuring lipase activity was used; FIG. 1 is a graph indicating the correlation when the substrate solution (iii) for measuring lipase activity was used; FIG. 1 is a graph indicating the correlation when the substrate solution (iv) for measuring lipase activity was used; and FIG. 1 is a graph indicating the correlation when the substrate solution (v) for measuring lipase activity was used.

Note that in FIGS. 1[1] to [5], the abscissa (x) represents the measurement results (measured values) of the lipase activity value of each sample as obtained by using the commercially available control reagent as described in the section 3.<2>. The measured values are represented in Unit/L.

Note that in FIGS. 1[1] to [5], the ordinate (y) represents the measurement results (measured values) of the lipase activity value of each sample as obtained by using the "measuring reagent containing each substrate solution for measuring lipase activity produced by the process of the present invention" as described in the section 3.<1>. The measured values are represented in Unit/L.

Here, in FIGS. 1[1] to [5], the samples of the "reference material" were depicted as "▲"; the samples of the "control serum-1" were each depicted as "○"; the samples of the "control serum-2" were each depicted as "□"; the samples of the "control serum-3" were each depicted as "●"; the samples of the "pooled serum" were each depicted as "◇"; and the samples of the "human serum" (the total of 50 specimens) were each depicted as "◆".

(2) Regression Formula of Correlation

The following illustrates the regression formula and correlation coefficient of correlation between the measurement results (measured values) as obtained using the "measuring reagent containing each substrate solution for measuring lipase activity produced by the process of present invention" as described in the above section 3.<1> and the measurement results (measured values) as obtained using the commercially available control reagent of the above section 3.<2> (Note that the "x" and "y" in the following regression formulas of correlation are as described in the above (1)).

[1] When the substrate solution (i) for measuring lipase activity was used as the substrate solution for measuring lipase activity produced by the process of the present invention, the regression formula of correlation was y=1.205x−7.999 and the correlation coefficient was $R^2$:0.9795.

[2] When the substrate solution (ii) for measuring lipase activity was used as the substrate solution for measuring lipase activity produced by the process of the present invention, the regression formula of correlation was y=1.136x−10.04 and the correlation coefficient was $R^2$:0.9892.

[3] When the substrate solution (iii) for measuring lipase activity was used as the substrate solution for measuring lipase activity produced by the process of the present invention, the regression formula of correlation was y=1.041x+1.756 and the correlation coefficient was $R^2$:0.9953.

[4] When the substrate solution (iv) for measuring lipase activity was used as the substrate solution for measuring lipase activity produced by the process of the present invention, the regression formula of correlation was y=1.1739x−11.93 and the correlation coefficient was $R^2$:0.9861.

[5] When the substrate solution (v) for measuring lipase activity was used as the substrate solution for measuring lipase activity produced by the process of the present invention, the regression formula of correlation was y=1.1065x−5.760 and the correlation coefficient was $R^2$:0.9980.

5. Discussion

FIGS. 1[1] to [5] and the regression formulas of correlation and values of the correlation coefficients as described in the above section 4.(2) demonstrate that even when the five kinds of the substrate solution for measuring lipase activity were used, any of them gave a good correlation between the measurement results (measured values) of the lipase activity in each sample, which values were calculated using the substrate solutions for measuring lipase activity produced by the process of the present invention, and the measurement results (measured values) of the lipase activity value as calculated using the commercially available control reagent.

This ascertains that the substrate solutions for measuring lipase activity produced in accordance with the process for producing a substrate solution for measuring lipase activity and the method for simplifying production of a substrate solution for measuring lipase activity according to the present invention can be used to accurately measure lipase activity in a sample.

Specifically, when the process for producing a substrate solution for measuring lipase activity and the method for simplifying production of a substrate solution for measuring lipase activity according to the present invention are used, the production of the substrate solution for measuring lipase activity can be made simple, less time-consuming, and low-cost. Besides, it has been demonstrated that the substrate solutions can provide accurate measurement results (measured values) of lipase activity in a sample.

The invention claimed is:

1. A process for producing a substrate solution that is used for measuring lipase activity in a sample and comprises, as a substrate for measuring lipase activity, 1,2-o-dilauryl-rac-glycero-3-glutaric acid (6'-methylresorufin) ester, the process comprising the steps of:

(1) mixing the substrate for measuring lipase activity directly with a silicone oil comprising polyoxyethylene/polyoxypropylene side-chains or a polyoxyethylene/polyoxypropylene condensate to prepare a mixture; and (2) mixing all or a portion of the mixture of step (1) with water or an aqueous solution.

* * * * *